(12) United States Patent
Dividino et al.

(10) Patent No.: US 12,100,514 B2
(45) Date of Patent: Sep. 24, 2024

(54) SYSTEM AND METHOD FOR VESSEL INFECTIOUS DISEASE IMPORTATION RISK ASSESSMENT

(71) Applicant: Global Spatial Technology Solutions Inc., Dartmouth (CA)

(72) Inventors: Renata Queiroz Dividino, St. Catharines (CA); Braeden John Medeiros, London (CA); Ana Luisa Alfaro Suzan, North York (CA); Dhivya Jayaraman, Halifax (CA); Benjamin Kurtis Friedrich, Halifax (CA)

(73) Assignee: Global Spatial Technology Solutions Inc., Dartmouth (CA)

( * ) Notice: Subject to any disclaimer, the term of this patent is extended or adjusted under 35 U.S.C. 154(b) by 661 days.

(21) Appl. No.: 17/204,471

(22) Filed: Mar. 17, 2021

(65) Prior Publication Data

US 2022/0301721 A1    Sep. 22, 2022

(51) Int. Cl.
| | |
|---|---|
| *G16H 50/30* | (2018.01) |
| *G08G 3/00* | (2006.01) |
| *G16H 10/60* | (2018.01) |
| *G16H 50/20* | (2018.01) |

(52) U.S. Cl.
CPC ............... *G16H 50/30* (2018.01); *G08G 3/00* (2013.01); *G16H 10/60* (2018.01); *G16H 50/20* (2018.01)

(58) Field of Classification Search
None
See application file for complete search history.

(56) References Cited

U.S. PATENT DOCUMENTS

| | | | |
|---|---|---|---|
| 9,779,594 B2 | 10/2017 | Rigdon et al. | |
| 10,394,776 B2* | 8/2019 | Khan | G16H 70/60 |
| 10,399,650 B2 | 9/2019 | Delay et al. | |
| 10,572,809 B1 | 2/2020 | Schurmann | |

(Continued)

OTHER PUBLICATIONS

Salinas et al., "DeepAR: Probabilistic Forecasting with Autoregressive Recurrent Networks", Amazon Research, Germany, Cornell University, Feb. 22, 2019, pp. 1-12 <https://arxiv.org/abs/1704.04110>.

(Continued)

*Primary Examiner* — Todd Melton
*Assistant Examiner* — Jason R Roberson
(74) *Attorney, Agent, or Firm* — BERESKIN & PARR LLP/S.E.N.C.R.L. s.r.l; Isis E. Caulder; Paul Blizzard

(57) ABSTRACT

Provided are systems and methods for vessel infectious disease importation risk assessment. This includes receiving vessel data from one or more sources, wherein the vessel data includes infectious disease data, determining a rendezvous history of the vessel based on the vessel data, determining a port visits history of the vessel based on the vessel data, determining the vessel disease burden based on the port visits history, the rendezvous history, the infectious disease data and a period of crew social exchange outside the vessel, determining the vessel disease progression dynamics based on the vessel disease burden and the vessel time of arrival at destination, and determining, at the processor, the infectious disease importation risk assessment associated with the vessel disease progression dynamics.

20 Claims, 12 Drawing Sheets

(56) References Cited

U.S. PATENT DOCUMENTS

| | | | |
|---|---|---|---|
| 11,342,051 B1* | 5/2022 | Jain | G16H 10/60 |
| 2015/0371182 A1 | 12/2015 | Lucas et al. | |
| 2017/0043848 A1 | 2/2017 | Rigdon et al. | |
| 2020/0184828 A1 | 6/2020 | Mazor et al. | |
| 2020/0264268 A1 | 8/2020 | Moore et al. | |
| 2020/0264296 A1 | 8/2020 | Dunagan et al. | |
| 2021/0295708 A1 | 9/2021 | Chung et al. | |
| 2022/0293282 A1* | 9/2022 | Lee | G16H 50/80 |
| 2022/0374797 A1 | 11/2022 | Kalinski | |

OTHER PUBLICATIONS

Wang, "Risk Assessment of the Overseas Imported COVID-19 of Ocean-Going Ships Based on AIS and Infection Data", ISPRS Int. J. Geo-Inf., May 27, 2020, 9(6), 351, pp. 1-14.

International Search Report and Written Opinion mailed May 10, 2022 in International Patent Application No. PCT/CA2022/050176 (7 pages).

Ding et al., "Incorporating Dynamic Flight Network in SEIR to Model Mobility between Populations", Appl Netw Sci, 2021, 6(1): 42 (pp. 1-24).

Chande et al., "Real-time, interactive website for US-county-level COVID-19 event risk assessment", Nat Hum Behav, 2020, 4: 1313-1319.

Böhning et al., "Estimating the undetected infections in the Covid-19 outbreak by harnessing capture-recapture methods", International Journal of Infectious Diseases, 2020, 97: 197-201.

Final Office Action mailed Nov. 14, 2022 in U.S. Appl. No. 17/171,516 (21 pages).

Advisory Action mailed Feb. 15, 2023 in U.S. Appl. No. 17/171,516 (5 pages).

Non-final Office Action mailed Mar. 20, 2023 in U.S. Appl. No. 17/171,516 (17 pages).

National Academies of Sciences, Engineering, and Medicine. 2003. Shipboard Automatic Identification System Displays: Meeting the Needs of Mariners—Special Report 273. Washington, DC: The National Academies Press. https://doi.org/10.17226/10708.

Clément Iphar, Aldo Napoli, Cyril Ray, Erwan Alincourt, David Brosset "Risk Analysis of falsified Automatic Identification System for the improvement of maritime traffic safety" 2016, Glasgow, United Kingdom. pp. 606-613—ISBN 978-1-138-02997-2. hal-01421905.

"Automatic identification system", Wikipedia, Feb. 3, 2021, pp. 6-8 <https://en.wikipedia.org/w/index.php?title=Automatic_identification_system&oldid=1004657806> (14 pages).

* cited by examiner

SYSTEM AND METHOD FOR VESSEL INFECTIOUS DISEASE IMPORTATION RISK ASSESSMENT

FIELD

The described embodiments relate to determining vessel infectious disease importation risk assessment, and specifically to analyzing vessel tracking data in order to determine the risk a vessel poses for a country or a port regarding the transmission and spread of infectious disease.

BACKGROUND

Global shipping poses many risks, including national security risks, risks related to communicable diseases, supply chain disruptions, and variable costs (including loading/unloading costs and insurance costs). Coast guard and naval resources are limited because the regions they are responsible for monitoring and protecting are very large, and not every vessel can be inspected.

Shipping vessels are tracked using vessel tracking devices such as Automatic Identification Systems (AIS) that include vessel-based transceiver systems. Each vessel transmits data including unique identification, position, course, and speed, amongst other things. The vessel may receive and display this information on an electronic chart display and information system (ECDIS). Shore-based tracking can include AIS base stations, and vessel traffic services (VTS) that may be provided at a harbor or port which provide functionality similar to air traffic control systems for aircraft.

AIS transceivers have been mandatory since the International Maritime Organization's (IMO) International Convention for the Safety of Life at Sea (SOLAS) for international voyaging ships with 300 or more gross tonnage (GT), and all passenger ships regardless of size. AIS has been implemented first as a terrestrial-based system (T-AIS) and later as a satellite-based system (S-AIS).

AIS data may be used to track vessels. AIS itself however, does not provide infectious disease risk information for a vessel. Additionally, AIS data does not provide risk protection for vessels which disable, spoof, or otherwise make malicious use of the transmitted data.

Communicable diseases may be transmitted between individuals in a variety of ways, including direct transmission, indirect transmission, droplet transmission, airborne transmission, fecal-oral transmission, and vector-borne transmission.

Direct transmission may include touching an infected individual, kissing, sexual contact, contact with oral secretions, or contact with body lesions.

Indirect transmission may include situations where a susceptible person is infected from contact with a contaminated surface. Some organisms (such as the Norwalk Virus, and COVID-19) are capable of surviving on surfaces for an extended period of time.

Droplet transmission may occur where the disease is transferred by infected droplets contacting surfaces of the eye, nose, or mouth. Droplets containing microorganisms can be generated when an infected person coughs, sneezes, or talks. Droplets can also be generated during certain medical procedures, such as bronchoscopy. Droplets are too large to be airborne for long periods of time, and quickly settle out of air.

Airborne transmission may occur in situations where droplet nuclei (such as residue from evaporated droplets) or dust particles containing microorganisms can remain suspended in air for long periods of time. Airborne transmission allows organisms to enter the upper and lower respiratory tracts.

Fecal-oral transmission may occur with organisms that infect the digestive system. Microorganisms may enter the body through ingestion of contaminated food and water. Inside the digestive system (usually within the intestines) these microorganisms multiply and are shed from the body in feces. If proper hygienic and sanitation practices are not in place, the microorganisms in the feces may contaminate the water supply through inadequate sewage treatment and water filtration. Fish and shellfish that swim in contaminated water may be used as food sources.

Vector transmission may include animals that are capable of transmitting diseases. Examples of vectors may include flies, mites, fleas, ticks, rats, and dogs. One common vector for disease is the mosquito, which transfers disease through the saliva which comes in contact with their hosts when they are withdrawing blood. Mosquitoes are vectors for malaria, West Nile virus, dengue fever, and yellow fever. Vectors may add an extra dimension to disease transmission, since vectors are mobile and may increase the transmission range of a disease.

Biting may not be the only way vectors can transmit diseases. Diseases may be spread through the feces of a vector. Microorganisms could also be located on the outside surface of a vector (such as a fly) and spread through physical contact with food, a common touch surface, or a susceptible individual.

Each of these methods of transmission poses risks for members of the crew, and raises the likelihood that a disease may be communicated from one geographical location to another aboard the vessel.

There is a need therefore for port authorities, national governments, public health organizations, and shipping companies to be able to quickly and accurately assess vessel infectious disease risk in order to identify vessels that may represent a threat to the port and to the country by virtue of the risk of communicable disease transmission.

For at least these reasons, there exists a need for an improved system and method for determining vessel infectious disease importation risk assessments.

SUMMARY

Risk assessments can be explored in different purposes/applications that can include: safety/health safety; inspection; insurance, including determinations of premiums; and logistics, including resource planning.

Infectious disease importation risk assessment prediction may determine the risk of a vessel to the population at a destination by virtue of the risk of the presence onboard of a communicable infectious disease.

The infectious disease may be introduced to the vessel in several different manners.

First, for each vessel there may be a period of time while at port, at anchorage, at dry-dock, etc. when the crew of the vessel has contact and social interactions with groups of people outside of the vessel. For example, a tanker vessel may be in port for a period of time while loading or unloading, and the crew may interact with non-crew persons at restaurants, bars, or other social environments. These external interactions may increase the risk of the communication of an infectious disease.

Second, a vessel may rendezvous with other vessels while at sea, for resupply, refueling. During these rendezvous at sea, crew members may interact with the crew of other vessels, and thereby may have external interactions at sea that may increase the risk of the communication of an infectious disease.

Third, a vessel may change crew members along its route, and thereby may have external crew onboard for a portion of its trip.

In a first aspect, there is provided a method for determining an infectious disease importation risk assessment associated with a vessel, the method comprising: receiving, at a processor, vessel data from one or more sources, wherein the vessel data includes infectious disease data; determining, at the processor, a rendezvous history of the vessel based on the vessel data; determining, at the processor, a port visits history of the vessel based on the vessel data; determining, at the processor, the vessel disease burden based on the port visits history, the rendezvous history, the infectious disease data and a period of crew social exchange outside the vessel; determining, at the processor, the vessel disease progression dynamics based on the vessel disease burden and the vessel estimated time of arrival at destination; and determining, at the processor, the infectious disease importation risk assessment associated with the vessel disease progression dynamics.

In one or more embodiments, the one or more sources may include a vessel information source, an AIS data source or a regional boundaries source.

In one or more embodiments, the method may further comprise generating, at the processor, enhanced AIS data included in the vessel data with region boundaries determined from a region boundaries data included in the vessel data; and tagging the enhanced AIS data based on vessel identification.

In one or more embodiments, determining the rendezvous history may comprise detection of unstable speed of the vessel based on the vessel data.

In one or more embodiments, the method may further comprise determining a vessel rendezvous in the rendezvous history by determining at least one route segment of the vessel, and identifying an outlier segment in the at least one route segment of the vessel.

In one or more embodiments, determining the port visits history may comprise classification of movement of the vessel based on the vessel data.

In one or more embodiments, the classification of movement may comprise classification into one of a moving class, a port visit class, an anchorage class, and a hop class.

In one or more embodiments, the determining the vessel disease burden may further comprise determining the vessel disease burden by correlating at least one selected from the group of the port class and the anchorage class, with the infectious disease data.

In one or more embodiments, the period of crew social exchange outside the vessel may be determined based on the rendezvous history, the port visits history and vessel crew member data included in the vessel data.

In one or more embodiments the method may further comprise: identifying one or more vessel crew changes in the vessel data; adjusting the period of crew social exchange outside the vessel according to the one or more vessel crew changes; and wherein the infectious disease importation risk assessment may be further determined based on the one or more vessel crew changes.

In a second aspect, there is provided a system for determining an infectious disease importation risk assessment associated with a vessel, the system comprising: a memory; a processor in communication with the memory, the processor configured to: receive vessel data from one or more sources, wherein the vessel data includes infectious disease data; determine a rendezvous history of the vessel based on the vessel data; determine a port visits history of the vessel based on the vessel data; determine a vessel disease burden based on the port visits history, the rendezvous history, the infectious disease data and a period of crew social exchange outside the vessel; determine the vessel disease progression dynamics based on the vessel disease burden and the vessel estimated time of arrival; and determine the infectious disease importation risk assessment associated with vessel progression dynamics.

In one or more embodiments, the one or more sources may include a vessel information source, an AIS data source or a regional boundaries source.

In one or more embodiments the processor may be further configured to: generate enhanced AIS data included in the vessel data with region boundaries determined from a region boundaries data included in the vessel data; and tag the enhanced AIS data based on vessel identification.

In one or more embodiments, the determining the rendezvous history may comprise detection of unstable speed of the vessel based on the vessel data.

In one or more embodiments, the processor may be further configured to: determine a vessel rendezvous in the rendezvous history by determining at least one route segment of the vessel, and identifying an outlier segment in the at least one route segment of the vessel.

In one or more embodiments, the determining the port visits history may comprise classification of movement of the vessel based on the vessel data.

In one or more embodiments, the classification of movement may comprise classification into one of a moving class, a port visit class, an anchorage class, and a hop class.

In one or more embodiments, the determining the vessel disease burden may further comprise determining the vessel disease burden by correlating at least one selected from the group of the port class and the anchorage class, with the infectious disease data.

In one or more embodiments, the period of crew social exchange outside the vessel may be determined based on the rendezvous history, the port visits history and vessel crew member data included in the vessel data.

In one or more embodiments, the processor may be further configured to: identify one or more vessel crew changes in the vessel data; adjust the period of crew social exchange outside the vessel according to the one or more vessel crew changes; and wherein the infectious disease importation risk assessment may be further determined based on the one or more vessel crew changes.

BRIEF DESCRIPTION OF THE DRAWINGS

A preferred embodiment will now be described in detail with reference to the drawings, in which.

DESCRIPTION OF EXEMPLARY EMBODIMENTS

Figure 1:
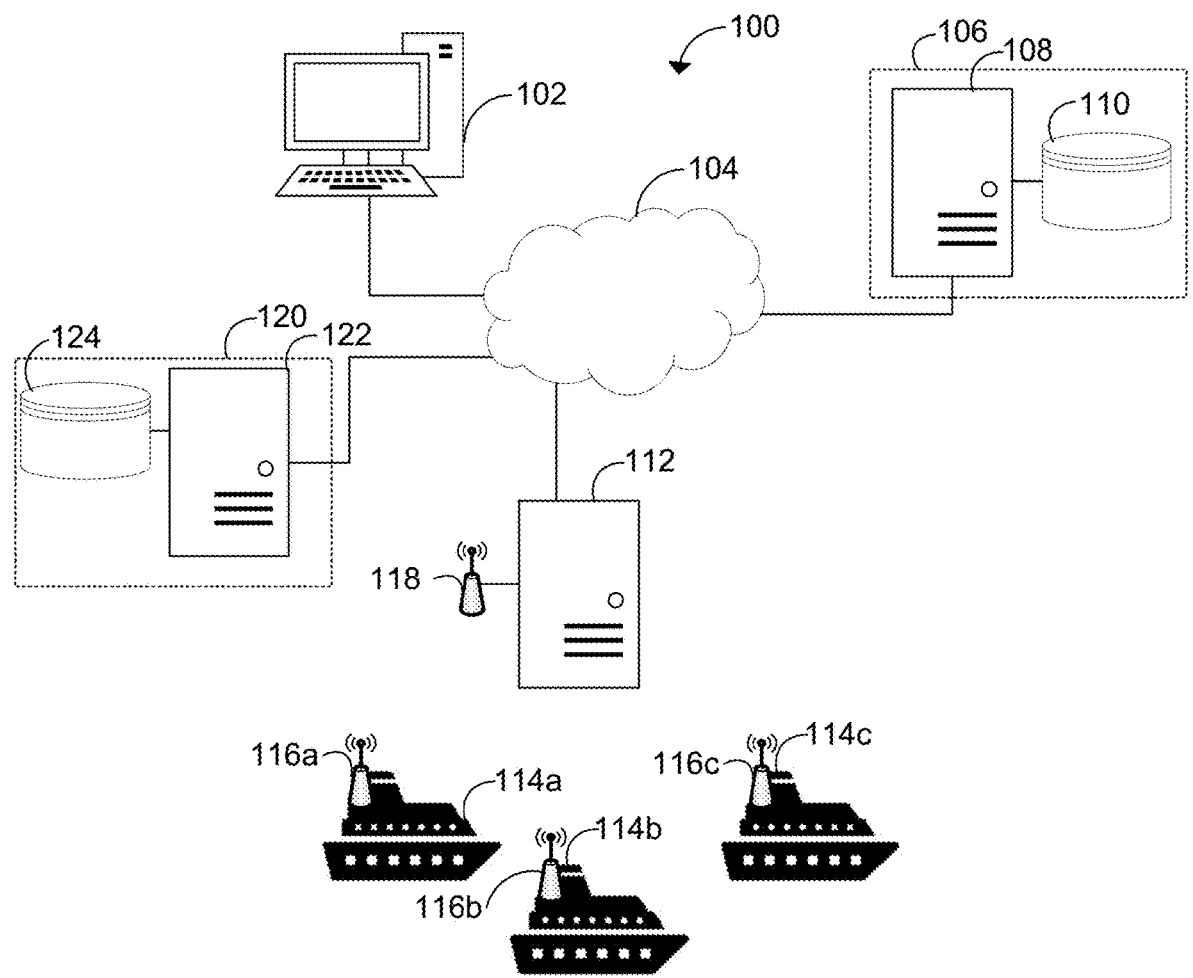
FIG. 1 shows a system diagram of a system for vessel infectious disease importation risk assessment in accordance with one or more embodiments.

It will be appreciated that numerous specific details are set forth in order to provide a thorough understanding of the example embodiments described herein. However, it will be understood by those of ordinary skill in the art that the embodiments described herein may be practiced without these specific details. In other instances, well-known methods, procedures and components have not been described in detail so as not to obscure the embodiments described herein. Furthermore, this description and the drawings are not to be considered as limiting the scope of the embodiments described herein in any way, but rather as merely describing the implementation of the various embodiments described herein.

It should be noted that terms of degree such as "substantially", "about" and "approximately" when used herein mean a reasonable amount of deviation of the modified term such that the end result is not significantly changed. These terms of degree should be construed as including a deviation of the modified term if this deviation would not negate the meaning of the term it modifies.

In addition, as used herein, the wording "and/or" is intended to represent an inclusive-or. That is, "X and/or Y" is intended to mean X or Y or both, for example. As a further example, "X, Y, and/or Z" is intended to mean X or Y or Z or any combination thereof.

The embodiments of the systems and methods described herein may be implemented in hardware or software, or a combination of both. These embodiments may be implemented in computer programs executing on programmable computers, each computer including at least one processor, a data storage system (including volatile memory or non-volatile memory or other data storage elements or a combination thereof), and at least one communication interface. For example and without limitation, the programmable computers (referred to below as computing devices) may be a server, network appliance, embedded device, computer expansion module, personal computer, laptop, personal data assistant, cellular telephone, smart-phone device, tablet computer, wireless device or any other computing device capable of being configured to carry out the methods described herein.

In some embodiments, the communication interface may be a network communication interface. In embodiments in which elements are combined, the communication interface may be a software communication interface, such as those for inter-process communication (IPC). In still other embodiments, there may be a combination of communication interfaces implemented as hardware, software, and a combination thereof.

Program code may be applied to input data to perform the functions described herein and to generate output information. The output information is applied to one or more output devices, in known fashion.

Each program may be implemented in a high level procedural or object-oriented programming and/or scripting language, or both, to communicate with a computer system. However, the programs may be implemented in assembly or machine language, if desired. In any case, the language may be a compiled or interpreted language. Each such computer program may be stored on a storage media or a device (e.g. ROM, magnetic disk, optical disc) readable by a general or special purpose programmable computer, for configuring and operating the computer when the storage media or device is read by the computer to perform the procedures described herein. Embodiments of the system may also be considered to be implemented as a non-transitory computer-readable storage medium, configured with a computer program, where the storage medium so configured causes a computer to operate in a specific and predefined manner to perform the functions described herein.

Furthermore, the systems, processes and methods of the described embodiments are capable of being distributed in a computer program product comprising a computer readable medium that bears computer usable instructions for one or more processors. The medium may be provided in various forms, including one or more diskettes, compact disks, tapes, chips, wireline transmissions, satellite transmissions, internet transmission or downloads, magnetic and electronic storage media, digital and analog signals, and the like. The computer useable instructions may also be in various forms, including compiled and non-compiled code.

Various embodiments have been described herein by way of example only. Various modifications and variations may be made to these example embodiments without departing from the spirit and scope of the invention, which is limited only by the appended claims. Also, in the various user interfaces illustrated in the figures, it will be understood that the illustrated user interface text and controls are provided as examples only and are not meant to be limiting. Other suitable user interface elements may be possible.

As recited herein, vessel tracking systems may include Automatic Identification Systems (AIS), and other such vessel tracking systems whether terrestrial-based or satellite-based.

As recited herein, abnormal behavior events and anomalies may be used interchangeably.

Reference is first made to FIG. 1, showing a system drawing 100 of a system for vessel infectious disease importation risk assessment. The system 100 has a user device 102, a network 104, an assessment service 106 having a server 108 and a database 110, at least one vessel tracking provider server 112 having a vessel tracking transceiver 118, at least one vessel 114 having a vessel tracking transceiver 116, and at least one infectious disease data provider 120 having an infectious disease server 122 and an infectious disease database 124.

User devices 102 may be used by an end-user to access an application (not shown) running on assessment service 106. For example, the application may be a web application, or a client/server application. The user devices 102 may be a desktop computer, mobile device or laptop computer. The user devices 102 may be in network communication with assessment service 106 via network 104. The user devices 102 may display the application and may allow a user to request a vessel assessment of at least one of the vessels 114. The end user may be from a government agency such as the Coast Guard, a public health organization, a defense organization such as the Navy, a corporate organization such as an international shipping company, or another interested party.

Network 104 may be a communication network such as the Internet, a Wide-Area Network (WAN), a Local-Area Network (LAN), or another type of network. Network 104 may include a point-to-point connection, or another communications connection between two nodes.

Assessment service 106 includes one or more servers 108 and one or more databases 110. Assessment service 106 may provide software services to the user device 102 and may communicate with at least one vessel tracking provider server 112 to receive vessel tracking data. The assessment service 106 may further communicate with other data providers (not shown), including $3^{rd}$ party data providers for vessel incident information, vessel information, regional boundary information, and vessel crime information.

Assessment service 106 may provide a web application that is accessible by the user devices 102. The web application may provide user authentication functionality as known, so that a user may create an account and/or log into the web application in order to request or receive vessel assessments. The assessment service 106 may provide the vessel assessment functionality to a user as described herein.

Assessment service 106 may implement an Application Programming Interface (API) to receive requests from the user devices 102, or from a third party (not shown). The assessment service 106 may reply to the API requests with API responses, and the API responses may provide the functionality of the web application provided by assessment service 106. The API may receive requests and send responses in a variety of formats, such as JavaScript Object Notation (JSON) or eXtensible Markup Language (XML).

The assessment service API may receive requests from an application running on the user devices 102. The application running on the user devices 102 may be downloaded from the web application provided at assessment service 106 or may be downloaded from the Google® Play Store or the Apple® App Store.

Server 108 is connected to network 104 and database 110 and may provide functionality as described herein. The server may implement one or more external APIs, as described above. The server 108 may be a physical server, may be the same server device as the device running the database 110, or may be provided by a cloud provider such as Amazon® Web Services (AWS).

Server 108 may have a web server provided thereon for providing web-based access to the software application providing the API and/or the software application providing the web application. The web server may be one such as Apache®, Microsoft® IIS®, etc. The software application providing the API and the web application may be Apache® Tomcat, Ruby on Rails, or another web application framework as known.

The database 110 is connected to network 104 and may store historical data for a number of vessels, including regional boundaries (including data received from an external data source, and data determined or generated by the assessment service itself), vessel tracking data (for example, including AIS data received from an AIS data vendor), vessel data (including vessel data received by a vessel data vendor), vessel incident data (including vessel incident data from a vessel incident data vendor), and vessel crime data (including vessel crime data from a vessel crime data vendor or knowledgebase).

The database 110 may further store historical vessel information including historical vessel Maritime Mobile Service Identity (MMSI) information, historical vessel name information, historical vessel port visit information, historical vessel trip information, historical vessel visit information, historical vessel trip movement information, historical vessel trip speed information, historical vessel tracking transmission information, historical vessel trip position accordance information, historical vessel trip sea route information, historical vessel trip crew size information, historical vessel incident information, and historical vessel rendezvous information. The database 110 may store other historical information such as historical vessel behavior tracking information and historical vessel abnormal behavior information.

The database 110 may further store generated profiles determined by the assessment service. The generated profiles include statistical information for vessels, including statistical information such as vessel Maritime Mobile Service Identity (MMSI) profiles, vessel name profiles, vessel destination profiles, vessel visit duration profiles, vessel trip duration profiles, vessel movement profiles, vessel speed profiles, vessel tracking transmission profiles, vessel tracking position accordance profiles, vessel sea route profiles, vessel crew size profiles, vessel incident profiles, and vessel rendezvous profiles. The statistical information in the generated profiles may be determined for each vessel, for a type of vessel (including size or manufacturer), or a combination of these factors. The database 110 may be a Structured Query Language (SQL) such as PostgreSQL or MySQL or a not only SQL (NoSQL) database such as MongoDB. For example, vessel profiles may include historical behavior change frequency distribution information as described herein.

Vessel tracking provider server 112 may be a first party server which is within the same organization as the assessment server 106, for example, a shore-based or satellite-based AIS receiver. Alternatively, the vessel tracking provider server 112 may be a third-party provider, such as exactEarth®, ORBCOMM®, Spacequest®, or Spire®. The assessment service 106 may receive vessel tracking data from multiple different vessel tracking provider servers 112.

The vessel tracking provider server 112 may have a vessel tracking transceiver 118 that receives vessel tracking transmissions of the at least one vessel 114. The vessel tracking transmissions may include a plurality of data as described herein about each vessel and its location. The vessel tracking provider may provide an API for the assessment service 106 to request periodic vessel tracking transmission data to be transferred. The vessel tracking provider may alternatively push vessel tracking transmission data to an API at the assessment service 106.

The vessel tracking provider server 112 may provide vessel tracking data in a plurality of formats and standards. In an exemplary embodiment, the vessel tracking provider server 112 may provide AIS data according to the International Maritime Organization (IMO) International Convention for the Safety of Life at Sea (SOLAS) treaty. The vessel tracking provider server 112 may perform pre-processing of vessel tracking data that is received by the vessel tracking transceiver 118.

As disclosed herein, vessel tracking data may allow ships and shore-based stations to view marine traffic in a geographical area. For example, the vessel tracking data may be displayed on a chartplotter. Alternatively, vessel tracking transceiver signals for a geographical area may be viewed via a computer using one of several computer applications such as ShipPlotter and Gnuais.

Vessel tracking transceiver 118 may demodulate the signal from a modified marine VHF radiotelephone tuned to the vessel tracking frequencies and convert into a digital format that the vessel tracking provider server 112 can read, store in memory, transmit over network 104, or display (not shown). The vessel tracking data received by vessel tracking transceiver 118 and vessel tracking provider server 112 may then be shared via network 104 using TCP or UDP protocols as are known.

The vessel tracking transceiver 118 may be limited to the collective range of the radio receivers used in the network as the vessel tracking provider system. In one embodiment, the vessel tracking provider system may have a network of shore-based vessel tracking transceivers to provide broader geographical coverage. In another embodiment, the vessel tracking provider system may have a network of satellite-based vessel tracking transceivers that may be used to receive vessel tracking transmissions from earth orbit.

Vessel tracking transceiver 118 may be a satellite receiver, or a dedicated VHF vessel tracking transceiver. The vessel tracking transceiver may receive AIS signals from local traffic for viewing on an AIS enabled chartplotter, or using an AIS compatible computer system. Port authorities or other shore-based facilities may be equipped with transceivers. Vessel tracking transceiver 118 may transmit in the Very High Frequency (VHF) range, with a transmission distance of about 10-20 nautical miles.

In the exemplary example of an AIS vessel tracking system, transceiver 118 may use the globally allocated Marine Band channels 87 and 88. AIS transceiver 118 may use the high side of the duplex from two VHF radio "channels" (87B) and (88B). For example, the AIS transceiver may use channel A 161.975 MHz (87B) and channel B 162.025 MHz (88B).

Vessel tracking transceiver 118 may provide information such as a vessel's identity, vessel type, vessel position, vessel course, vessel speed, vessel navigational status and other vessel safety-related information automatically to appropriately equipped shore stations, other ships and aircraft. Vessel tracking transceiver 118 may receive automatically such information from similarly fitted ships, may monitor and track ships; and may exchange data with shore-based facilities.

At least one vessel 114 may carry an AIS transceiver according to SOLAS regulation V/19—Carriage requirements for shipborne navigational systems and equipment. This regulation requires that AIS transceivers be fitted aboard all ships of 300 gross tonnage and upwards engaged on international voyages, cargo ships of 500 gross tonnage and upwards not engaged on international voyages and all passenger ships irrespective of size. The vessels 114 may be a variety of different types of vessels, including sailboats, shipping vessels, motorboats, yachts, passenger vessels, ferries, etc. There may be some vessels not required under SOLAS regulation who elect to fit AIS transceivers anyways.

Vessel tracking transceivers 116 aboard vessels 114 may function the same as vessel tracking transceiver 118, but may be designed for operation on a vessel (i.e. sizing, electrical power requirements, etc.). Further, each vessel 114 may transmit its location using its corresponding vessel tracking transceiver 116. This may allow vessels to provide their location to other vessels to ensure awareness and visibility of their vessel.

Infectious disease service 120 includes one or more servers 122 and one or more databases 124. Infectious disease service 120 may be a first party, or a third-party service that may collect and store disease infection information about one or more diseases and may communicate with assessment service 106. There may be many infectious disease services 120, for example, one per geographical region. The infectious disease service 120 may be provided by, for example, a public health organization of a country, the World Health Organization, or an educational institution.

Infectious disease service 120 may include information such as confirmed cases of an infectious disease and transmission rate (i.e., rate per 1,000,000 population) for one or more infectious diseases. Public Health Ontario, for example, publishes such data. The Government of Canada, including Health Canada, has a set of surveillance data as well which may include other surveillance data.

Some infectious disease data may be updated daily, monthly, or yearly.

For example, for COVID-19 disease importation risk assessment, infectious disease services may include: the Johns Hopkins University (JHU) Coronavirus Resource Center, Our World in Data (OWID)—Coronavirus, amongst others.

Both infectious disease services, OWID and JHU, are updated daily. The ingestion of the infectious disease data from the infectious disease services at 432 may also occur every day subsequent to the updating of the infectious disease service. The data received from the infectious disease services may include the number of confirmed cases, number of recovered cases, number of deaths, test positive rate, etc. collected for the past day.

Infectious disease service 120 may provide a web application that is accessible via network 104. The web application may provide reporting access to the infectious disease data stored in database 124. The assessment service 106 may scrape data from the web application provided by infectious disease service 120.

Alternatively, infectious disease service 120 may implement an Application Programming Interface (API) to receive requests from the assessment service 106. The infectious disease service 120 may reply to the API requests with API responses, and the API responses may provide the infectious disease data to assessment service 106. The API may receive requests and send responses in a variety of formats, such as JavaScript Object Notation (JSON) or eXtensible Markup Language (XML).

Server 122 is connected to network 104 and database 124 and may provide infectious disease data as described herein. The server 122 may implement one or more external APIs, as described above. The server 122 may be a physical server, may be the same server device as the device running the database 124, or may be provided by a cloud provider such as Amazon® Web Services (AWS).

The database 124 is connected to network 104 and may store historical infectious disease data for a jurisdiction. The infectious disease data may include a breakdown of reported infectious disease cases by sub-regions within the jurisdictions, for example, if the infectious disease data is for a country, then the sub-regions may include states, provinces, cities, postal or zip codes, or other geographical identifiers.

The infectious disease data in database 124 may be, for example, the Johns Hopkins University COVID-19 dataset provided by the Coronavirus Resource Center. Other examples may include aggregated data sources such as the World Health Organization (WHO), European Centre for Disease Prevention and Control (ECDC), US Center for Disease Control (CDC). Other examples may include subnational departments of health such as the Washington State Department of Health, Maryland Department of Health, New York State Department of Health, New York City Health Department, NYC Department of Health and Mental Hygiene, etc.

The database 124 may further store infectious disease incidence rates, infectious disease case counts, infectious disease deaths, etc. The data in database 124 may include cases grouped by time period, for example, reported cases per day, month, or year.

The database 124 may be a Structured Query Language (SQL) such as PostgreSQL or MySQL or a not only SQL (NoSQL) database such as MongoDB. For example, vessel profiles may include historical behavior change frequency distribution information as described herein.

Figure 2:
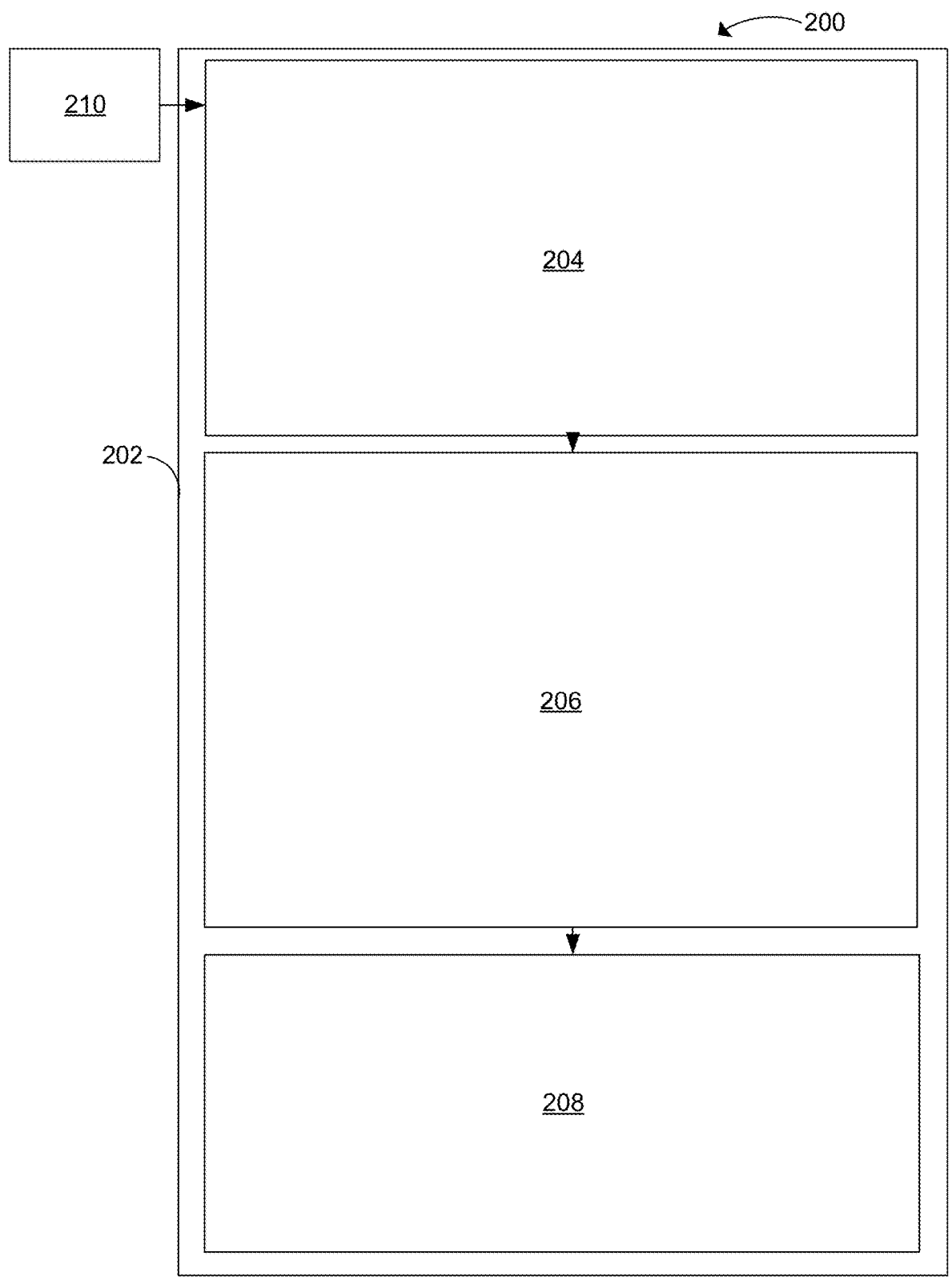
FIG. 2 shows a method diagram for determining a vessel infectious disease importation risk assessment in accordance with one or more embodiments.

Referring next to FIG. 2, there is shown a method 200 for determining a vessel infectious disease importation risk assessment in accordance with one or more embodiments. Method 200 may be a high-level method that is described in further detail herein. Method 200 may be performed by server 202, having data ingestion 204, vessel data and infectious data processing 206, and vessel infectious disease risk analysis 208.

One or more data sources 210 may be provided as input to the assessment server 202. These one or more data sources may include one or more vessel tracking data providers, one or more vessel information providers, one or more mapping providers, one or more regional boundary providers, etc.

The data from the one or more data sources 210 is received by a data ingestion 204. The data ingestion process is described in further detail in FIG. 3. The ingested data is received by vessel data and infectious disease processing 206, which is described in further detail in FIG. 4. The processed data is received by vessel risk analysis 208, which is described in more detail in FIG. 5.

Figure 3:
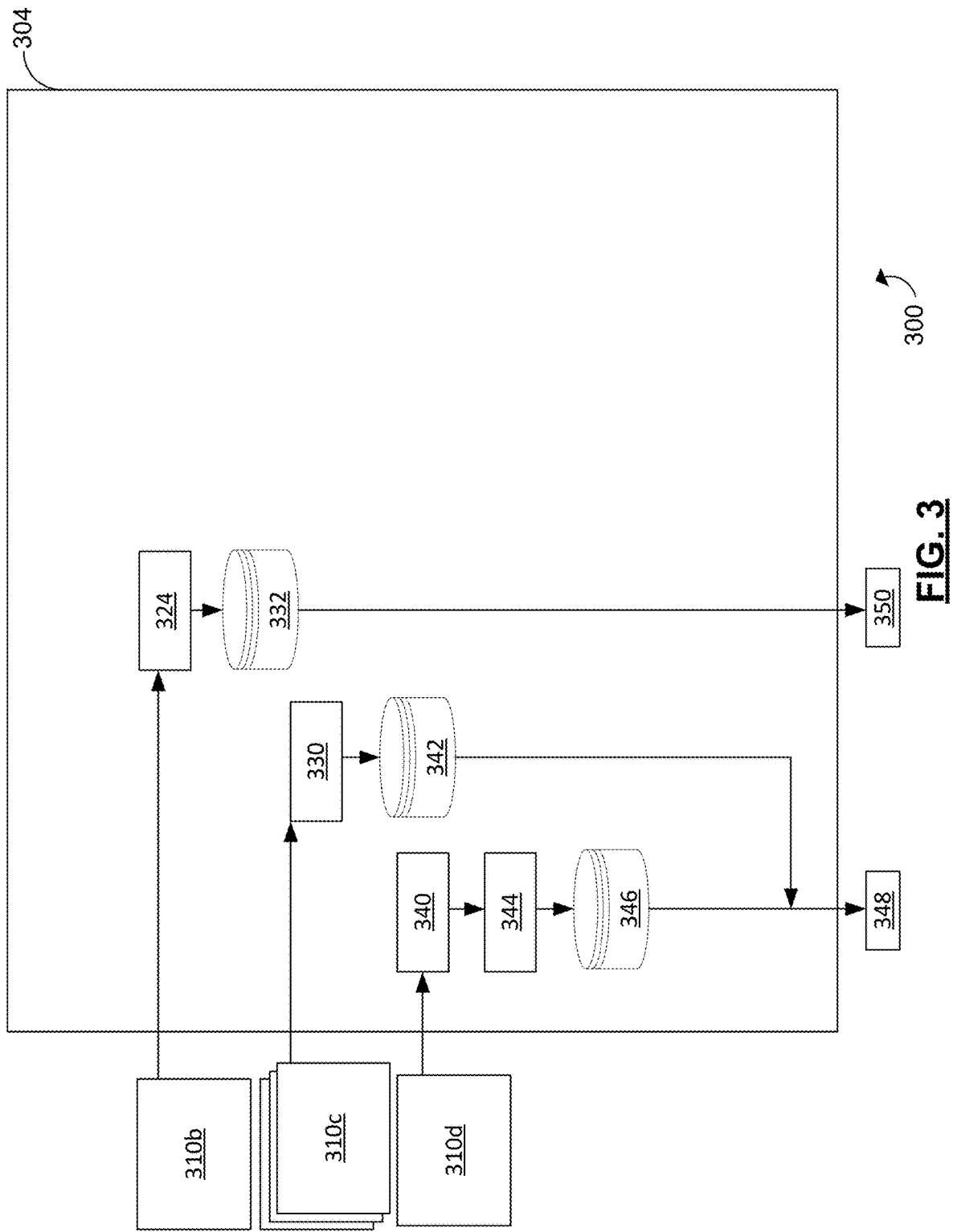
FIG. 3 shows a method diagram for ingesting data in accordance with one or more embodiments.

FIG. 3 shows a data ingestion method 300 provided by assessment server 304 in accordance with one or more embodiments. The data ingestion method may receive data from one or more data sources, one or more vessel information data providers 310*b*, one or more vessel tracking data providers 310*c*, and one or more region boundary data providers 310*d*. Data ingestion may occur periodically, i.e. daily, weekly, monthly, or may occur generally in real-time.

Data ingestion 300 may be performed to receive data into data lakes and may use a data streaming service such as Amazon® Web Services (AWS®) Firehose Kinesis®. Data may be ingested in near real-time or using a periodic polling process.

Vessel information data is received from the one or more vessel information data providers 310*b* at vessel data ingestion 324. The vessel information data providers may be a database such as the National Maritime Information Database (NM ID) from the Canadian Government, the Information Handling Services (IHS) vessel database, the Spectrum Direct Database provided by Industry Canada/ITU.

The vessel information data may include vessel name information, vessel crew information (including but not limited to, changes in vessel crew manifests, crew member nationality, etc.), vessel general classification information, vessel individual classification information (including classification history), a vessel station group MMSI, a vessel gross tonnage, vessel passenger capacity information, vessel length, vessel MMSI number, vessel registration information including applicant information of the vessel registration, vessel ownership information (for example, the corporation of legal entity e.g. Groenewald & Germishuys CC, Tangming Co Ltd), etc. The vessel information data, once processed by vessel data ingestion 324, may be stored in vessel database 332. The vessel database 332 may be stored at database 110 (see FIG. 1). The vessel database 332 may provide vessel data 350 to the vessel data processor and the infectious disease risk analysis engine.

Vessel tracking data is received from the one or more vessel tracking data providers 310*c* for vessel tracking data ingestion 330. This may include satellite-based or terrestrial-based tracking data.

In an exemplary embodiment, AIS data is received from the one or more AIS data providers 310*c* at AIS data ingestion 330. As described above, the AIS data may include Satellite AIS data (SAIS) and Terrestrial AIS data (TAIS). The AIS data may be stored as point data, corresponding to the periodic transmissions of an AIS equipped vessel.

Vessel tracking data may be processed by vessel tracking data ingestion 330 and may be decoded from a raw format. The processed vessel tracking data may be stored in the AIS database 342.

In an exemplary embodiment, AIS data may be processed by AIS data ingestion 330 and may be decoded from the AIS National Marine Electronics Association (NMEA) 0183 or NMEA 2000 data formats. The decoding may further include decoding AIS sentences such as AIVDM sentences. Decoding of AIS messages may further include decoding based on ITU Recommendation M.1371 (including revisions), IALA Technical Clarifications on Recommendation ITU-R M.1371-1, and IEC-PAS 61162-100. An AIVDM sentence may describe the vessel position and vessel information of a vessel, or other pieces of information as described in the AIS specifications. The processed AIS data may be stored in the AIS database 342.

The vessel tracking data ingestion 330 may determine variables from each vessel tracking data point or segment of vessel tracking data for a vessel.

The vessel tracking data ingestion 330 may further match vessels identified in the vessel tracking data with vessels found in the vessel database 332 or vessel incident database 326.

The vessel tracking database 342 may be stored at database 110 (see FIG. 1). The vessel tracking data from vessel tracking database 342 may be provided with the region boundary data from region boundary database 346 as vessel tracking data and boundary data 348 to the vessel processing (see FIG. 4) and the risk analysis engine (see FIG. 5).

Regional boundary data is received from the one or more region boundary data providers 310*d* at region boundary data ingestion 340. The region boundary ingestion 340 may involve pre-processing of the region boundary data. Region boundary data curation 344 may be performed automatically, or manually, in order to connect disparate region boundaries in the region boundary data. The region boundary data may include a plurality of connected points, where each point has latitude and longitude data. The points may further be connected using the geometric location of ports, marine regions, and locations of Exclusive Economic Zones (EEZ). The region boundaries may be encoded in a shapefile. A shapefile may be a simple, nontopological format for storing the geometric location and attribute information of geographic features. Geographic features in a shapefile may be represented by points, lines, or polygons (areas).

Marine regions and EEZs may be provided as shapefiles. The marine region and EEZ shapefiles may be, for example, those produced by Flander Marine Institute which maintains a database of international borders in open waters. At 344, the shapefiles may be altered or curated. For example, an EEZ may be altered further to improve data processing times by reducing the size of the shapefile. The curation 344 may be performed by generating a one-way buffer in land for the EEZ. This may simplify the geometry around the coastline and allow joining of vessel tracking messages that may be at the land-sea boundary. The buffering of only 1 side may prevent an increasing of the extent of a countries EEZ.

The port shapefiles may be determined using the World Port Index ports. The ports may be converted into points, and then buffered to generate port zone shapefiles.

After the regional boundary data curation 344 is complete, the curated regional boundary data may be stored in region boundary database 346. The region boundary database 346 may be provided by database 110 (see FIG. 1). The region boundary database 346 may provide the curated region boundary data 348 to the vessel data processor and the infectious disease risk analysis engine.

Figure 4:
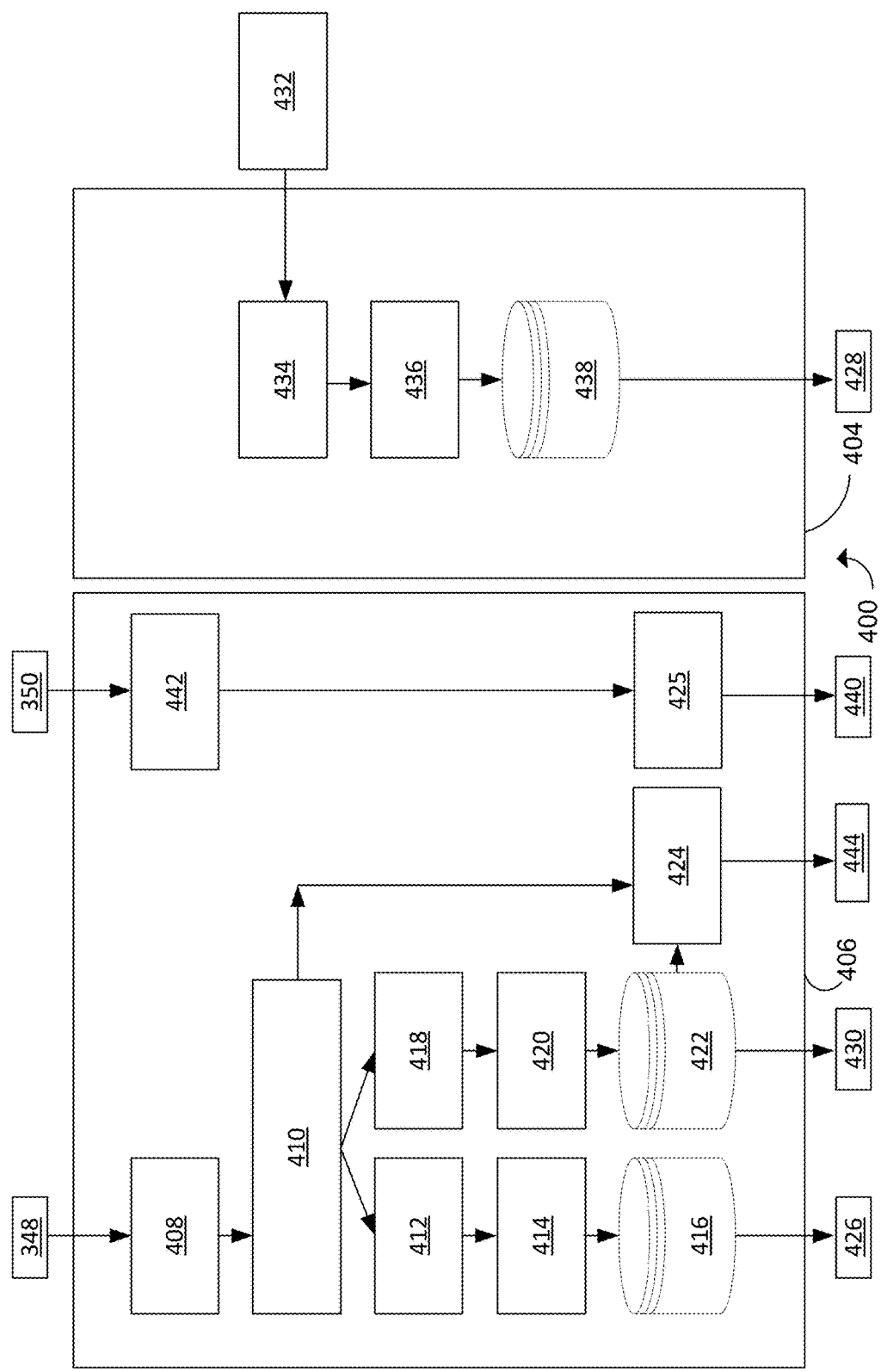
FIG. 4 shows a method diagram for processing vessel data and infectious disease data in accordance with one or more embodiments.

Referring next to FIG. 4, there is shown a method 400 for processing vessel data and infectious disease data in accordance with one or more embodiments. The method 400 may run at a vessel data processor 406 and disease data processor 404 and may receive vessel tracking data and boundary data 348, and vessel data 350 from the data ingestion. Infectious disease data 428 may be provided to the infectious disease risk engine.

Figure 11:
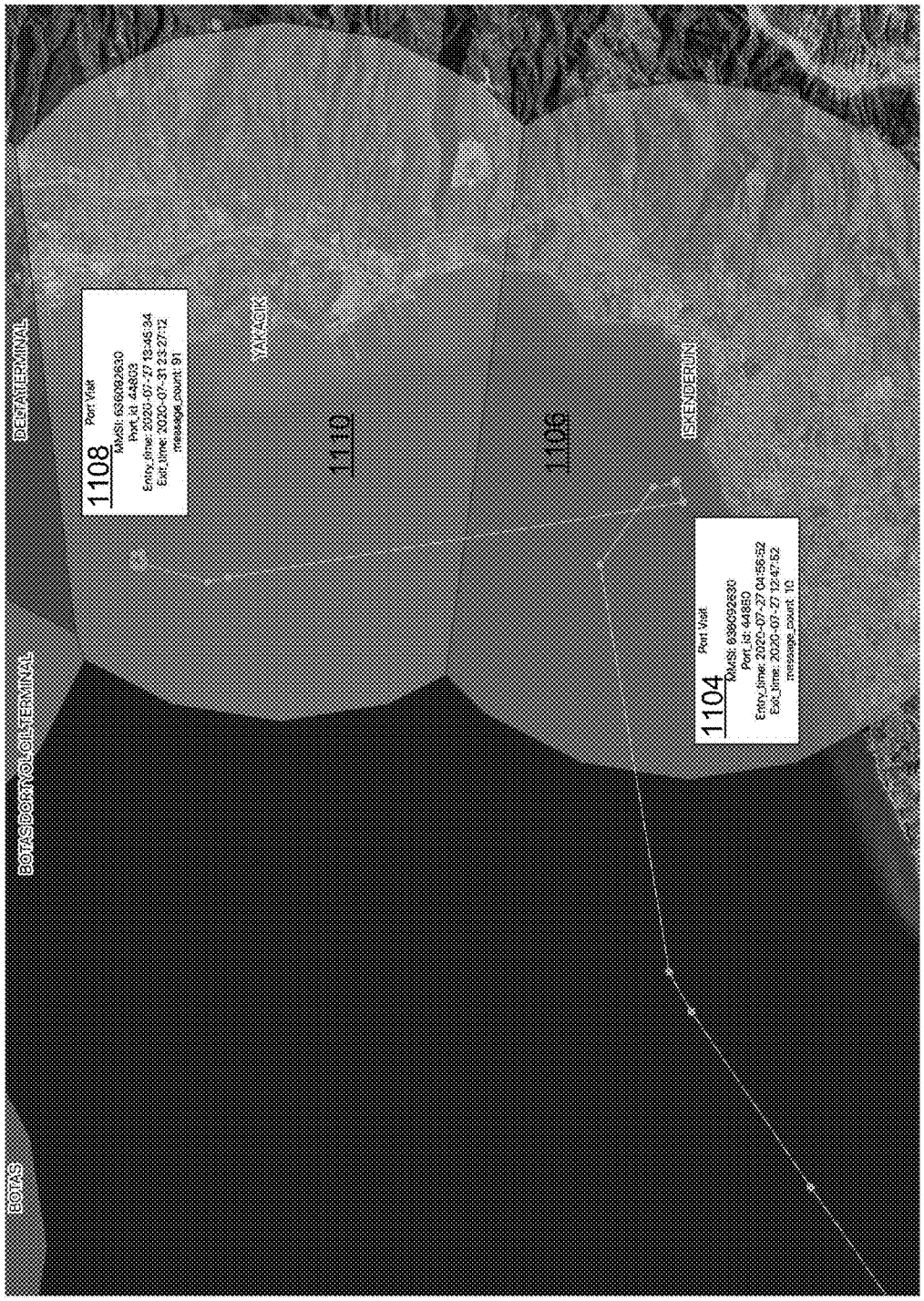
FIG. 11 shows a map diagram for port visit identification in accordance with one or more embodiments.

At 408, the vessel tracking data 346 is enhanced with boundary data 348. The join operator between the shapefiles and vessel tracking positions may output the corresponding location identification on which each vessel tracking message is being reported in. This information can then be used by later modules for selecting region specific analysis. FIG. 11 shows an example of the identified regions and ports.

The vessel data enhancement may be performed using the following method.

First, a shapefile (nontopological format for storing geometric location and attribute information of geographic features) is received including geometric location of ports, marine regions, and Exclusive Economic Zones (EEZ). Geographic features in a shapefile can be represented by points, lines, or polygons (areas).

Next, a one-way buffer is determined inland for the EEZ. The buffer may simplify the geometry around the coastline as well as allowing joining of vessel tracking messages that may be on the land boundary.

Next, a plurality of port points from a plurality of port shapefiles are determined and buffered.

Next, one or more position points are received and joined with the buffer.

At 410, one or more vessels may be identified in the vessel tracking data and boundary data. The vessels may be identified by determining a unique vessel signature and assigning a corresponding unique vessel identifier based on the unique vessel signature. The unique vessel identifier may be an internal identifier of the vessel assessment system, and each segment may have a unique vessel identifier associated with it. Alternatively, an MMSI number may be determined, or a vessel name may be detected or matched, or by another means of identification as is known. The identification may include assigning a unique vessel identifier to data points or segments, creating a unique vessel identifier to assign to the data points or segments, or updating an existing unique vessel identifier for the data points of segments.

At 412, segments having unstable speed may be identified from the one or more segments. This may include identifying segments for a vessel underway at sea where the vessels speed falls outside of the average for the trip or is otherwise inconsistent with other segments.

At 414, vessel rendezvous' may be identified from the one or more segments based on the unstable speed determinations from 412. The vessel rendezvous may be decoded from the vessel tracking data in the one or more segments.

The identified vessel rendezvous from the one or more segments may be stored in a vessel rendezvous history database 416. The vessel rendezvous history database may be provided by database 110 (see FIG. 1). The vessel rendezvous history in vessel rendezvous history database 416 may be associated with the unique vessel identifier.

The vessel rendezvous data in the vessel rendezvous history database 416 may include the identity of one or more vessels involved in the rendezvous, a location at sea where the rendezvous occurred, a maritime zone where the rendezvous occurred, a start time and an end time of the rendezvous. Further, the rendezvous data may also include information about services or goods transferred between the vessels involved with the rendezvous.

Figure 8:
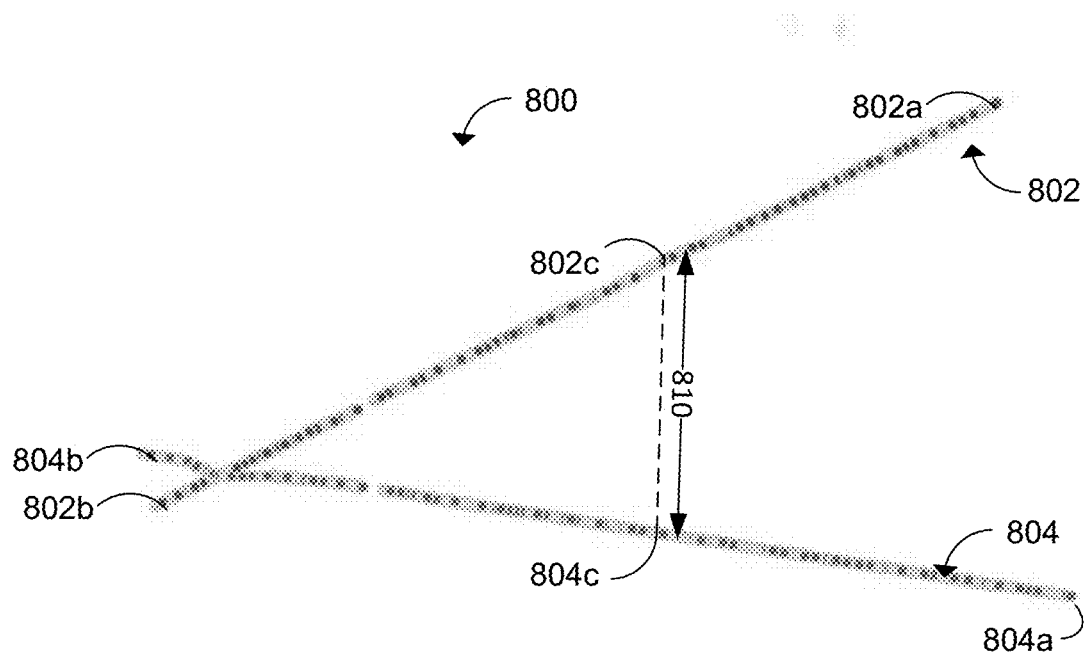
FIG. 8 shows a map diagram for two vessels engaged in a rendezvous in accordance with one or more embodiments.
Figure 9:
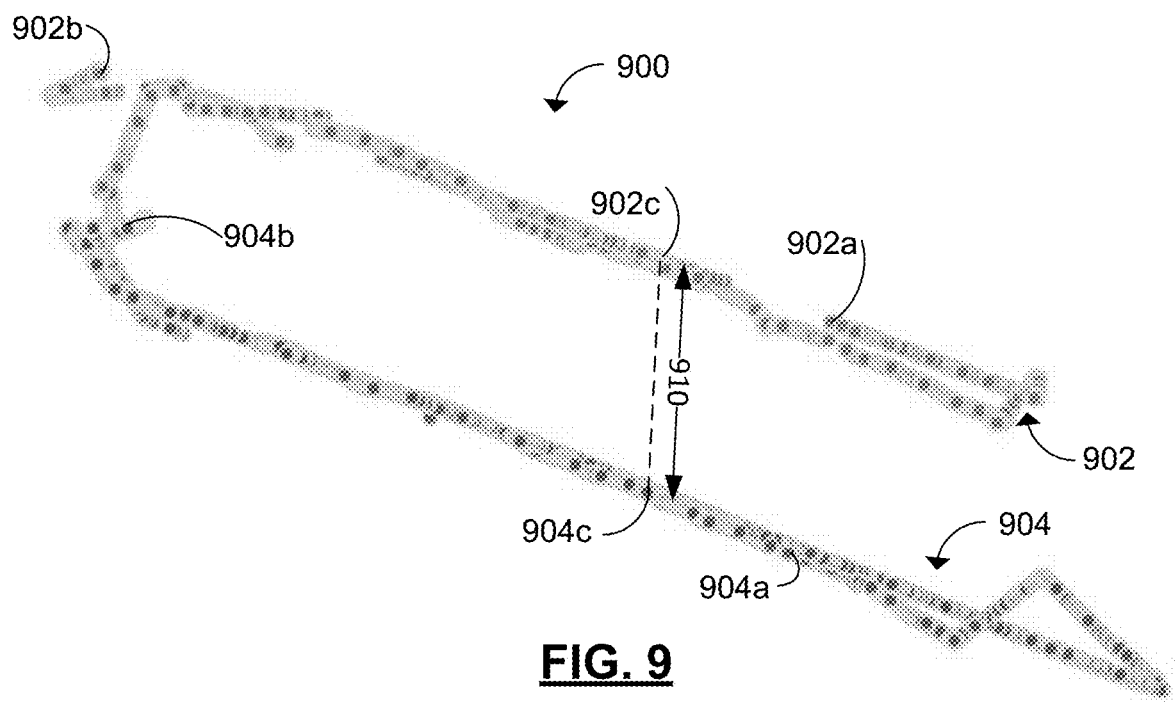
FIG. 9 shows a map diagram for two vessels loitering in the same vicinity in accordance with one or more embodiments.
Figure 10:
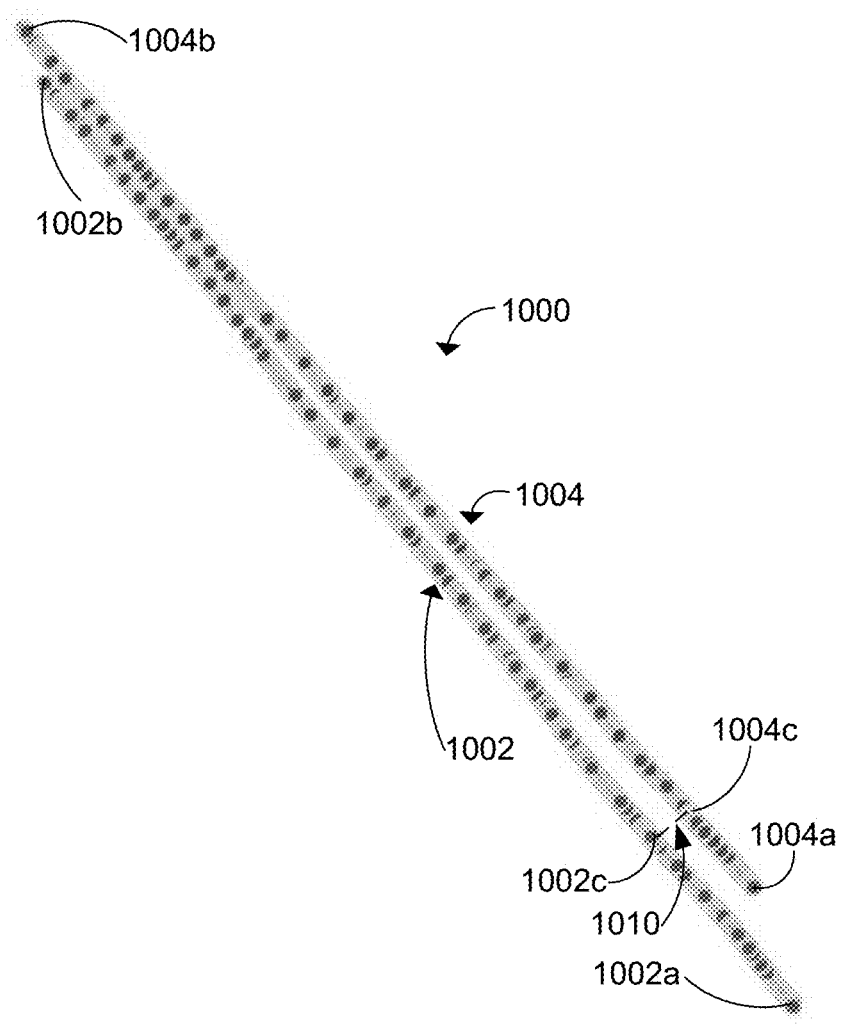
FIG. 10 shows a map diagram for two vessels engaged in a parallel course rendezvous in accordance with one or more embodiments.

Vessel rendezvous may include a path crossing, such as shown in FIG. 8, two vessels loitering in the same vicinity as shown in FIG. 9, and a parallel course as described in FIG. 10. Other patterns of vessel rendezvous may also be identified and the vessels involved identified as involved in a rendezvous. While two vessels are shown in the same vicinity, there may be more than two vessels involved.

The vessel rendezvous history may be provided to the infectious disease importation risk assessment at 426.

At 418, a vessel behavior pattern classification may be performed. This may include determining a port visit by joining a vessel tracking data point or segment with a boundary. This enhancement may occur for many segments of a trip for a vessel, for each data point, or for particular portions of the data corresponding to a vessel. This may further include classifying data points based on a vessel movement classification. For example, each data point or segment may be classified as "moving", "port", "anchorage", "hop". The classification of the data points or segments may be used to identify the state of the vessel with respect to its movement. Further, each data point or trip may be classified based on a trip movement classification, including trip stop and go points, for example, stopped or moving. The trip movement classification may be for determining when and where the trip of the vessel starts and ends, including matching the start and the end with the region or port information. For example, the vessel has a very low speed and moves somewhat (approximately ~300 m) then it may be classified as 'at anchor'. Further, if the vessel moved very little (approximately less than ~50 m) then the vessel may be classified as 'berthed'.

At 418, data points may be classified. The classification may be implemented using a finite state machine. The vessel tracking data may include positional information (latitude, longitude) which may be used to generate inferred states of the vessel (i.e. that the vessel is either in a static or transition state). For a grouping of vessel tracking data (i.e. a segment) to be considered static, a plurality of vessel tracking data showing the vessel position remaining within a small squared area is required. Once the vessel tracking data has been labelled as static or transition the inferred states may be further labelled based on the probability of switching between a static and transition state. This may permit further vessel movement classification states such as 'anchor', 'port', 'hop', and 'moving'. From these states a hop may be a small distance transition that takes place in between two static groups of messages. This may include identifying several sequential data points corresponding to movement during a vessel trip, i.e. "moving" classification where the vessel is underway between its origin and its destination. The "moving" classification may be based on the location of the vessel and its speed, which may be decoded from the vessel tracking data in the one or more segments. Port classifications may be determined by identifying sequential data points corresponding to the vessel arriving at and sitting docked in port, i.e. the "port" class. Anchorage classifications may be made by identifying sequential data points corresponding to the vessel parked in anchorage, i.e. the "anchorage" class, where the vessel is anchored. Hop classifications may be a short port visit between the port of origin and the final destination port or anchorage.

In another example, a vessel segment may be classified as a 'hop' which includes small groupings of movement between stop points such as ports. These smaller trip segments ("hops") may be used to segment a vessel trajectory into smaller segments.

The vessel tracking data may be segmented or grouped into segments based on a time period, or in an exemplary embodiment the segments may be determined based on the vessel behavior pattern classification.

This segmentation may be based on time periods (for example, each segment may represent one hour of vessel tracking data for a particular vessel).

In an exemplary embodiment, segmentation may be based on movement classification as described herein, for example, a segment may be determined based on one trip point (such as a port) to another trip point (such as another port). Vessel movement classification is described further at 418. The vessel movement classification may further segment trips between ports into smaller segments as required, for example, for a fishing vessel which may take a particular zig-zag pattern while trawling at sea.

The vessel tracking data may be stored as raw vessel tracking data in vessel tracking database 342. The vessel tracking data may be grouped for each vessel into segments, or into individual trips (i.e. port to port). Optionally, each trip may be further segmented into time period segments as described above.

This may include (but is not limited to) determining distance travelled, speed, acceleration, jerk, bearing, and bearing rate.

The individual trip segments may be further augmented by extracting features from the data for each segment including one or more points, known as point features. The point features may include distance travelled, speed, acceleration, jerk, bearing, and bearing rate.

Further, at 418, statistical information about a data point, or a trip segment may be determined as disclosed herein. The statistical information may include average, mean, mode, minimum, maximum values for a data point or segment.

For a segment of vessel tracking data, statistics based on the vessel tracking data points may be determined including maximum, minimum, mean, median, standard deviation, and the 10th, 25th, 75th and 90th percentiles for the vessel tracking reported speed for each vessel and at different ocean regions. The statistics may also be determined for the distance travelled, acceleration, jerk, and bearing rate (or any other determined statistic) in addition to speed.

At 420, a port visit may be identified or detected from the one or more segments received from 418. This may involve determining from the one or more segments, the location of the port, the duration of the stay, and other relevant data based on the vessel's stay at the port. A port visit is characterized by the final destination port of a vessel trip. This may be described in further detail in FIG. 11.

The identified port visits from the one or more segments may be stored in a vessel visit history database 422. The vessel visit history database may be provided by database 110 (see FIG. 1). The vessel visit history in vessel visit history database 422 may be associated with the unique vessel identifier.

The port visit data in vessel visit history database 422 may include a port identifier, a time of arrival, a time of departure, a listing of cargo unloaded or loaded during the visit, a listing of crew changes to the vessel, etc.

At 424, the vessel port visit history from 422 and the vessel signature from 410 may be used to determine an estimated time of arrival for the vessel. The estimated time of arrival may be an estimated time of arrival at a future destination based on the port visit history and the vessel signature. The estimated time of arrival may be provided to the infectious disease importation risk assessment at 444.

At 442, vessel crew size and max occupancy may be determined based on the vessel data 350 received from ingestion. The vessel crew and max occupancy determination 442 may be provided by the vessel data 350 directly or it may be indirectly determined based on the size of vessel, shipbuilder identification, cargo or passenger capabilities, etc.

At 425, vessel crew size may be identified or decoded from the one or more segments along in the vessel data 350 and may be further determined based on the vessel type determination 442. The vessel crew size may be decoded from the vessel data 350 and the vessel tracking data in the one or more segments. The crew size data determined from the vessel data 350 may include crew manifest changes (for example when a crew member joins or leaves a vessel), temporary crew manifest changes (for example, when a temporary captain comes aboard for navigation through a particular area), and passenger manifest changes. For example, for a given vessel, the crew manifest may be determined and the number and identity of the crew aboard the vessel may be tracked in case members leave, are added, or are replaced at points along a vessel's voyage.

The identified vessel crew size from the one or more segments may be stored in the vessel crew size history database (not shown). The vessel crew size history database may be provided by database 110 (see FIG. 1). The vessel crew size history in the vessel crew size history database may be associated with the unique vessel identifier.

At 432, an infectious disease provider may provide infectious disease information. This may include infectious disease data from one or more infectious disease services 120 (see FIG. 1).

At 434, data provided by the one or more infectious disease services may be combined and enhanced into a single data set. From each provider, the raw data may include the number of infected individuals, number of recovered individuals, number of deaths, and positive testing rate. Other geographical information and metadata may be used to enhance the data from the one or more infectious disease services.

At 436, disease burden is determined. The disease burden within the reported case numbers of a national or sub-national public health agency may not reflect the reality of the true number of cases since there exists a vast proportion of asymptomatic infected subjects including those with mild symptoms among all infected individuals who are not detected.

At disease burden determination 436, a scaled system was developed to determine a true number of cases that includes both official reporting and also undetected or asymptomatic cases which are unreported. The scaling parameters to determine the true case counts are as follows.

The first step is a determination of cases which are being missed (i.e. as they are asymptomatic). This may be achieved using a capture-recapture method to determine a lower bound estimate for infected but undetected subjects in a population.

Capture-recapture methods, as are known, use the capture history of individuals to estimate those who have never been caught. The method may use the frequencies of those caught once and those caught twice. These additional cases are added to the data reported by the country. From the total number of infected, recovered, deaths and the calculated hidden cases, a total number of active cases for each country is determined.

Additionally, with regard to testing, test positivity rates may be used to compensate for inadequate testing (high positivity=low testing) to arrive at a final predicted true case count. This may be achieved using a multiplicative factor which may be used to multiply the number of reported cases by a public health agency plus the number of asymptomatic cases. The testing information may be used later in 508.

For each national, sub-national, or other geographic area available in the infectious disease data 432 from infectious disease provider 120 (see FIG. 1), the raw infectious disease data as well as the infectious disease burden data determined at 436 may be stored in the infectious disease database 438. The infectious disease data in infectious disease database 438 may be provided to the risk processor at 428.

Figure 5:
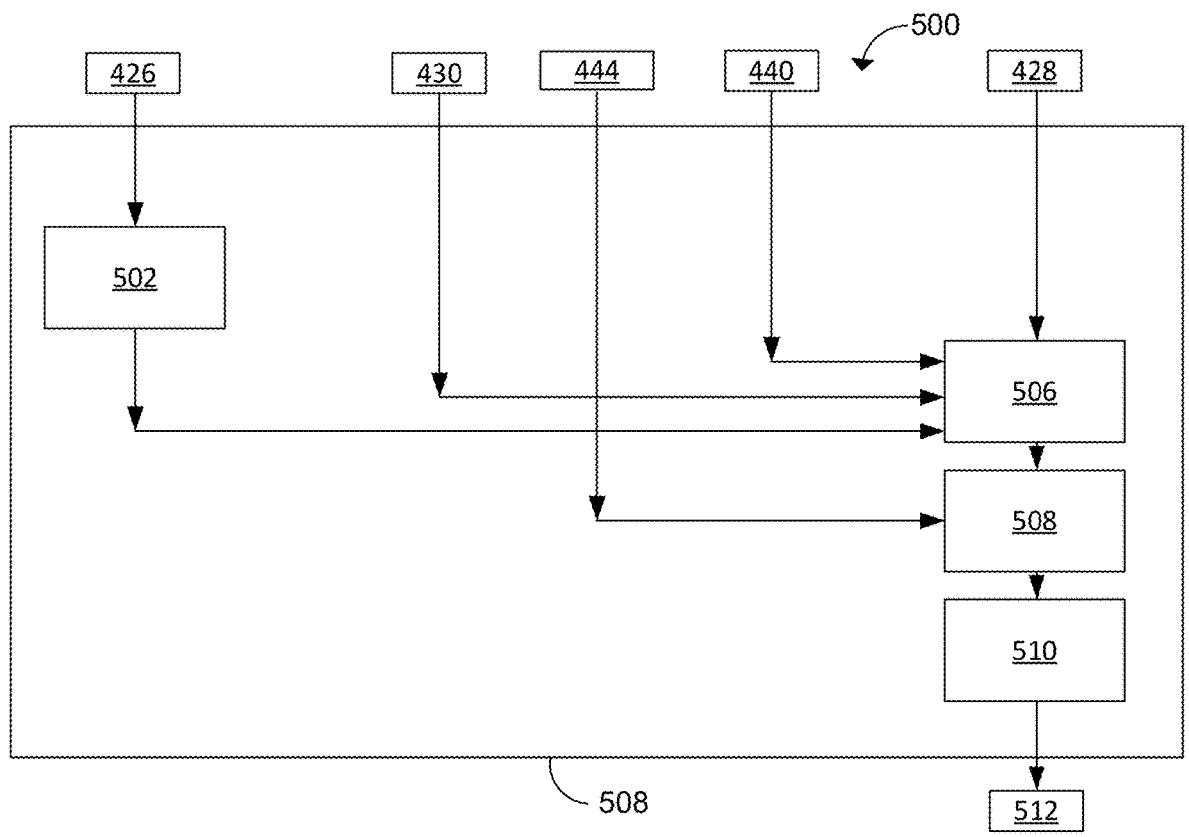
FIG. 5 shows a method diagram of analyzing vessel infectious disease risk in accordance with one or more embodiments.

Referring next to FIG. 5, there is shown a method diagram 500 for analyzing vessel infectious disease risk in accordance with one or more embodiments. Vessel rendezvous history 426, vessel port visit history 430, vessel crew member history 440, and infectious disease data 428 may be received from the vessel data processor.

At 502, the rendezvous history 426 is received. The rendezvous history 426 for a vessel may be used in order to determine a potential period of crew social exchange outside the vessel. This detection reflects a factor of the crew's interactions with other crew via rendezvous at sea. The rendezvous determination 502 generates information including the unique identifier (such as MMSI, or a generated identifier) of the vessels involved, the distance between the vessels during the rendezvous and the time interval of the rendezvous. Based on the distance and time interval, a probability may be determined that describes the likelihood that the rendezvous included some crew social interaction. A threshold may be used such that only rendezvous with higher probability are considered, i.e. the two vessels were very close to each other and remain close for a long time interval.

For example, a vessel rendezvous may include a path crossing, such as shown in FIG. 8, two vessels loitering in the same vicinity as shown in FIG. 9, and a parallel course as described in FIG. 10. Other patterns of vessel rendezvous may also be identified and the vessels involved identified as involved in a rendezvous. While two vessels are shown in the same vicinity, there may be more than two vessels involved.

In determining the potential period of crew social exchange during a rendezvous 502, portions of a vessel's route may be considered along a common timeframe with another vessel's route. This may include determining a minimum distance and a duration for individual segments of a vessel's route, or determining a distance for each point in a set of points between one vessel and another, and summing the product of the distance metric and the time between each point.

For any two vessels, the minimum required duration time and minimum required distance may be determined, which may be a condition for the two vessels to execute and concretize a rendezvous. The minimum required time and distance may be based on the vessels' dimensions and type. The method may determine the total time spent by any two vessels in proximity where their distance is closer than a minimum required distance threshold. The larger the total time spent by the two vessels, the greater the likelihood that a rendezvous with social exchange (e.g., crew exchange, goods exchange) has occurred. The vessel rendezvous assessment may be provided to the infectious disease importation risk assessment at 426.

At 506, the rendezvous with social exchange history determined at 502, the vessel port visit history 430, the crew information 440 are received, and the vessel disease burden is determined. This may be done by estimating the number of exposed individuals in the crew during a port visit or rendezvous.

For example, if the vessel visited a port, the number of exposed individuals in the crew during the port visit may be estimated. This may be performed based on the information about disease burden in a country given by the enhanced disease data sources (see 428).

An adapted binomial probability model may be adapted to determine the vessel disease burden during a port visit. The model may determine the risk that one or more individuals is infected with an infectious disease such as SARS-CoV-2 associated with social gatherings. This model may predict the number of exposed by calculating r, where $r=1-(1-p)^n$, where p is the probability of infection (active cases/population) multiplied by an ascertainment bias (a constant of 10 for countries where testing is low (positivity rate >10%) and 5 for countries with adequate testing (positivity <10%)) and n is number of crew.

In another example, if the vessel has rendezvoused another vessel, the vessel disease burden may be determined by calculating the number of exposed individuals in the crew during the rendezvous may be estimated.

A binomial probability model may be adapted to determine the vessel disease burden during a rendezvous. The model outputs the risk that one or more individuals is infected with an infectious disease such as SARS-CoV-2. This model may be used to predict number of exposed by calculating r, where $r=1-(1-p)^n$, p is the probability of infection (total active cases of both vessels/total vessel population including both vessels) and n is total number of both vessels' crew.

Once the information about the vessel disease burden during a port visit or rendezvous is determined (e.g. at 506), the disease progression dynamics at the vessel may be determined (e.g. at 508).

At 508, the infectious disease progression dynamics in the vessel population may be modelled. This may include modelling the infectious disease with variants of the classical Susceptible, Infected and Recovered (SIR) model and the Susceptible, Exposed, Infected and Recovered (SEIR) model. The information about the current size of exposed, infected and recovered individuals in the population may be updated based on the information about vessel disease burden (calculated in 506) during a port visit or rendezvous.

The differential equations of SEIR model may be modified to determine the vessel disease progression dynamics. The model includes demographics dynamics derived from the vessel network. This modified SEIR model is called vessel-SEIR that may account for the dynamic vessel network and incorporates mobility between vessel crew into the epidemiological modelling. Vessel-SEIR models how individuals that are exposed to an infectious disease may spread the disease to other individuals during the vessel trip to its destination. The movements of exposed individuals between the vessel and the port visits or rendezvous may be modelled. Exposed individuals in the crew may travel in and out of the vessel and therefore the crew population may change over time. An exposed individual may either be infected by an infectious individual during a port visit or rendezvous, or within the same population in a vessel.

Taking information about where the vessel has been (i.e. the port visits) and what it has done on its journey (i.e. the rendezvous) may update parameters used by the SE IR model. The SEIR model may be used to determine how a communicable disease will progress over time. Vessel-SEIR outputs the size of exposed, infected, and recovered populations at current location and once the vessel reaches its target port.

At 510, once the total number of infected and exposed crew members (at current location and at destination) has been calculated in 508, the combination of these values may be mapped into a risk score between 0 and 1 (0 being no-risk, 1 being high-risk).

This mapping may be calibrated by the user and may be user configurable. Some users may consider that a vessel with any exposure of the crew to the disease as a high-risk, and therefore receive a high-risk assessment (i.e. the vessel should be flagged for investigation and/or the crew tested for the infectious disease). In another example, other users may consider only vessels that are predicted to have at least one infected crew onboard to considered as high-risk, and therefore receive a high-risk assessment.

The vessels may be presented in a user interface colored by assessment risk score (green for low-risk to red for high-risk). When the user selects a vessel at the user interface, the user may see the vessel's risk assessment score as well as the total number of infected and exposed crew members onboard.

The risk assessment output 512 may be a probability of a vessel being assessed a risk. The probability may be mapped to a classification value, and a plurality of classification values may be used to describe a vessel's risk assessment. For example, a vessel may have a risk assessment selected from "very high", "high", "medium", "low", "none". Different classifications and different classification scales may be used.

The vessel risk assessment 512 may be used for different purposes. The risk assessment may allow for simulation of a vessel's environment, route, or piloting decisions in order to identify risks. The vessel risk assessment 512 may be used in order to identify the likelihood of a vessel arriving on time according to a predetermined schedule. For example, the schedule may relate to contractual obligations including the vessel arriving at a destination by a certain time, scheduling of port resources such as cranes, scheduling of vessel or port personnel, and availability of equipment.

The risk assessment 512 may represent the likelihood of a risk activity (e.g., importation of infectious disease into a country via maritime traffic).

Figure 6:
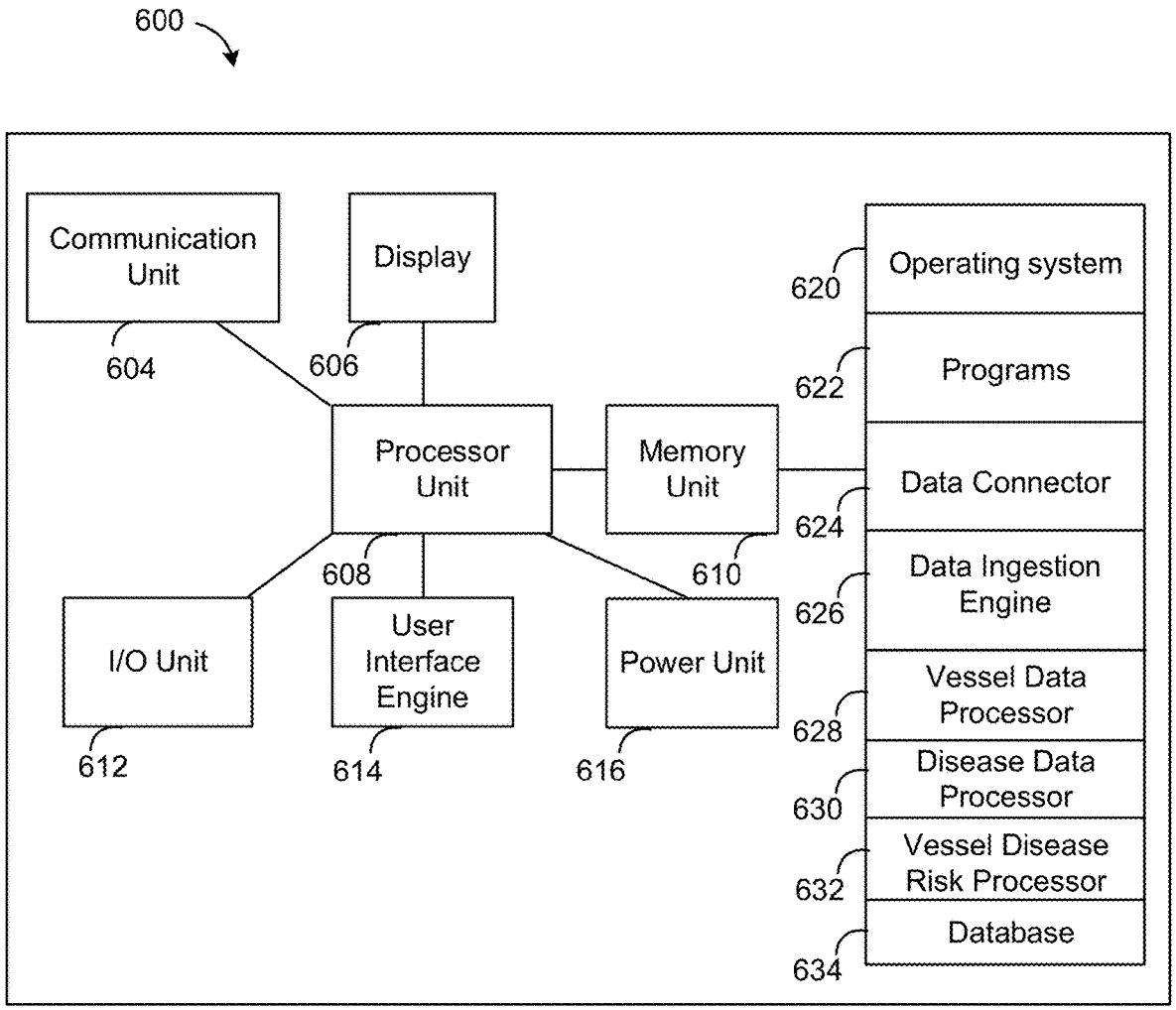
FIG. 6 shows a device diagram of a server in accordance with one or more embodiments.

Referring next to FIG. 6, a device 600 of a server is shown in accordance with one or more embodiments. The server 600 may be the server 108 of remote server 106 (see FIG. 1).

The server 600 has communication unit 604, display 606, I/O unit 612, processor unit 608, memory unit 610, user interface engine 614, and power unit 616. The memory unit 610 has operating system 620, programs 622, data connector 624, data ingestion engine 626, vessel data processor 628, disease data processor 630, vessel disease risk processor 632 and database 634. The processing server 600 may be a virtual server on a shared host or may itself be a physical server.

The communication unit 604 may be a standard network adapter such as an Ethernet or 802.11x adapter. The processor unit 608 may include a standard processor, such as the Intel Xeon processor, for example. Alternatively, there may be a plurality of processors that are used by the processor unit 608 and may function in parallel. Alternatively, there may be a plurality of processors including a Central Processing Unit (CPU) and a Graphics Processing Unit (GPU). The GPU may be, for example, from the GeForce® family of GPUs from Nvidia®, or the Radeon® family of GPUs from AMD®. There may be a plurality of CPUs and a plurality of GPUs.

The processor unit 608 can also execute a user interface engine 614 that is used to generate various GUIs, some examples of which are shown and described herein, such as in FIGS. 12, 13, 14, and 15. The user interface engine 614 provides for vessel risk assessment layouts for users to configure, request, review, and respond to vessel risk assessments, and the information submitted using these interfaces may be processed by the data ingestion engine 626, vessel data processor 628, disease data processor 630, vessel disease risk processor 632 and database 634. User interface engine 614 may be provided as an Application Programming Interface (API) or a Web-based application that is accessible via the communication unit 604.

I/O unit 612 provides access to server devices including disks and peripherals. The I/O hardware provides local storage access to the programs running on processing server 600.

The power unit 616 provides power to the processing server 600.

Memory unit 610 may have an operating system 620, programs 622, data connector 624, data ingestion engine 626, vessel data processor 628, disease data processor 630, vessel disease risk processor 632 and database 634.

The operating system 620 may be a Microsoft Windows Server® operating system, or a Linux-based operating system, or another operating system.

The programs 622 comprise program code that, when executed, configures the processor unit 608 to operate in a particular manner to implement various functions and tools for the processing server 600.

Data connector 624 may provide for integration, either push or pull with one or more vessel tracking provider servers 112 (see FIG. 1), and one or more $3^{rd}$ party data providers (such as vessel data or vessel information providers, one or more mapping providers, one or more regional boundary providers, one or more vessel incident providers, and one or more infectious disease services—also referred to herein as one or more infectious disease data providers). The integration may be an API integration as known, for example using an XML based REST API. The data connector 624 may transmit and receive requests and responses to the one or more vessel tracking provider servers and the one or more $3^{rd}$ party data providers using the communication unit 604.

Data ingestion engine 626 may receive data from the data connector 624, and may ingest and pre-process data from the one or more vessel tracking provider servers and the one or more $3^{rd}$ party data providers, as described in FIG. 3. The ingested data may be stored in database 634 and processed by vessel data processor 628.

Vessel data processor 628 may provide the functionality of data processor 406 and may receive data from the data ingestion engine 626 and from the database 634, and may determine a vessel rendezvous history, a vessel port visit history, vessel estimated time of arrival predictions, and vessel crew numbers as described in FIG. 4. The vessel data processor 628 may send the determined parameters to the vessel disease risk processor 632, and may store them in the database 634.

Disease data processor 630 may receive infectious disease data from one or more infectious data providers (see e.g. 432 in FIGS. 4 and 120 in FIG. 1), either directly or by querying database 634. The disease data processor 630 may provide the functionality of disease data processor 404.

Vessel disease risk processor 632 may receive disease data from disease data processor 630, and vessel data from vessel data processor 628, and may determine vessel infectious disease importation risk assessments as described in FIG. 5.

Optionally, database 634 may be hosted by server 600. The database may correspond to the database 110 (see FIG. 1). In an alternate embodiment, the database may run on a separate server from the server 600 and may be available via communication unit 604.

Figure 7:
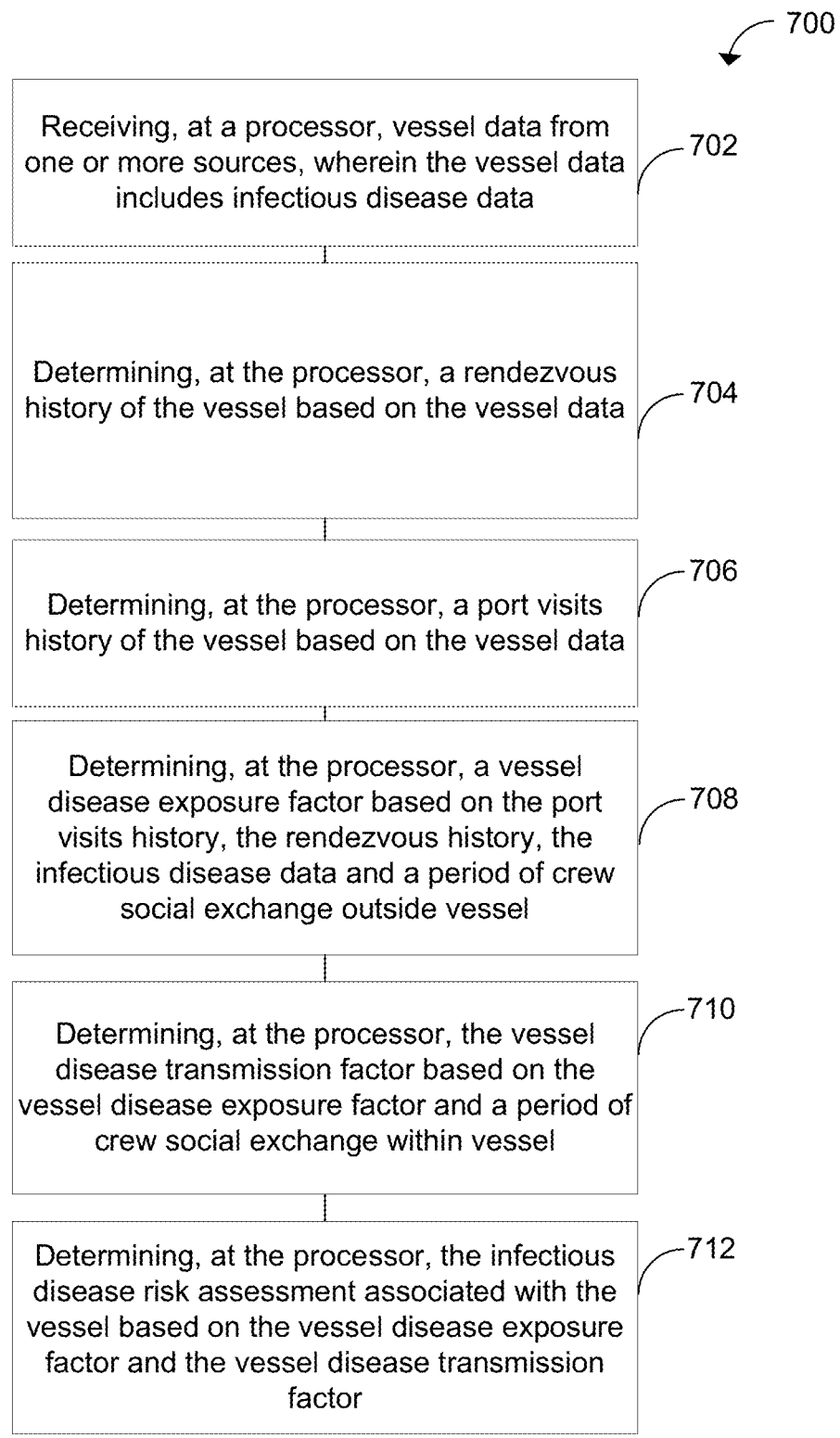
FIG. 7 shows a method diagram for determining a vessel infectious disease importation risk assessment in accordance with one or more embodiments.

Referring next to FIG. 7, there is shown a method 700 for determining a vessel infectious disease importation risk assessment in accordance with one or more embodiments.

At 702, receiving, at a processor, vessel data from one or more sources, wherein the vessel data includes infectious disease data.

At 704, determining, at the processor, a rendezvous history of the vessel based on the vessel data.

At 706, determining, at the processor, a port visits history of the vessel based on the vessel data.

At 708, determining, at the processor, a vessel disease burden based on the port visits history, the rendezvous history, the infectious disease data and a period of crew social exchange outside vessel.

At 710, determining, at the processor, the vessel disease progression dynamics based on the vessel disease burden and the vessel estimated time of arrival at destination.

At 712, determining, at the processor, the infectious disease importation risk assessment associated with the vessel disease progression dynamics.

Optionally, the one or more sources may include a vessel information source, an AIS data source or a regional boundaries source.

Optionally, the method may further comprise: generating, at the processor, enhanced AIS data included in the vessel data with region boundaries determined from a region boundaries data included in the vessel data; and tagging the enhanced AIS data based on vessel identification.

Optionally, the determining the rendezvous history may comprise detection of unstable speed of the vessel based on the vessel data.

Optionally, the method may further comprise: determining a vessel rendezvous in the rendezvous history by determining at least one route segment of the vessel, and identifying an outlier segment in the at least one route segment of the vessel.

Optionally, the determining the port visits history may comprise classification of movement of the vessel based on the vessel data.

Optionally, the classification of movement may comprise classification into one of a moving class, a port visit class, an anchorage class, and a hop class.

Optionally, the determining the vessel disease burden may further comprise determining the vessel disease burden by correlating at least one selected from the group of the port class and the anchorage class, with the infectious disease data.

Optionally, the period of crew social exchange outside the vessel may be determined based on the rendezvous history, the port visits history and a vessel crew member data included in the vessel data.

Optionally, the method may further comprise: identifying one or more vessel crew changes in the vessel data; adjusting the period of crew social exchange outside the vessel according to the one or more vessel crew changes; and wherein the infectious disease importation risk assessment may be further determined based on the one or more vessel crew changes.

Referring next to FIG. 8, there is shown a map diagram 800 for two vessels engaged in a rendezvous in accordance with one or more embodiments. The rendezvous detection 404 (see FIG. 4) and determination of crew social exchange 502 (see FIG. 5) may identify rendezvous events of a vessel and may incorporate the rendezvous events in order to determine crew member exposure to an infectious disease.

A first vessel may follow track or route 802 and a second vessel may follow track or route 804. Two vessels may navigate, and rendezvous while each is along a route. The received vessel tracking data for the detected rendezvous for the first vessel may begin at 802a and end at 802b, and for the second vessel may begin at 804a and end at 804b. The series of points along the first vessel route 802 may correspond to the same time frame as second vessel route 804.

The rendezvous detection 414 (see FIG. 4) may identify the series of points in the route 802 and 804 as indicative of a rendezvous between the first vessel and the second vessel.

The determination of crew social exchange 502 (see FIG. 5) may determine a risk factor for the rendezvous based on the determined risk assessment of each vessel, the time spent by each vessel in proximity to the other vessel, and the distance between the two vessels (for example, distance 810). The determination may include a summation of risk for each point in the first vessel track 802 with a corresponding point in second vessel track 804.

Referring next to FIG. 9, there is shown a map diagram 900 of two vessels loitering in the same vicinity in accordance with one or more embodiments. Two vessels may remain in close proximity while crew transfer occurs, and the rendezvous may involve both vessels loitering while rendezvous takes place. The rendezvous detection 404 (see FIG. 4) and determination of crew social exchange 502 (see FIG. 5) may identify rendezvous events of a vessel, and may incorporate the rendezvous events in order to determine crew member exposure to an infectious disease.

A first vessel may follow track or route 902 and a second vessel may follow track or route 904. The received vessel tracking data for the detected rendezvous for the first vessel may begin at 902a and end at 902b, and for the second vessel may begin at 904*a* and end at 904*b*. The series of points along the first vessel route 902 may correspond to the same time frame as second vessel route 904.

The rendezvous detection 414 (see FIG. 4) may identify the series of points in the route 902 and 904 as indicative of a rendezvous between the first vessel and the second vessel.

The determination of crew social exchange 502 (see FIG. 5) may determine a risk factor for the rendezvous based on the determined risk assessment of each vessel, the time spent by each vessel in proximity to the other vessel, and the distance between the two vessels (for example, distance 910). The determination may include a summation of risk for each point in the first vessel track 902 with a corresponding point in second vessel track 904.

Referring next to FIG. 10, there is shown a map diagram 1000 of two vessels engaged in a parallel course rendezvous in accordance with one or more embodiments. Two vessels may travel in a parallel course while crew transfer occurs, and the rendezvous may involve both vessels moving together in a parallel fashion. The rendezvous detection 404 (see FIG. 4) and determination of crew social exchange 502 (see FIG. 5) may identify rendezvous events of a vessel, and may incorporate the rendezvous events in order to determine crew member exposure to an infectious disease.

A first vessel may follow track or route 1002 and a second vessel may follow track or route 1004. The received vessel tracking data for the detected rendezvous for the first vessel may begin at 1002*a* and end at 1002*b*, and for the second vessel may begin at 1004*a* and end at 1004*b*. The series of points along the first vessel route 1002 may correspond to the same time frame as second vessel route 1004.

The rendezvous detection 414 (see FIG. 4) may identify the series of points in the route 1002 and 1004 as indicative of a rendezvous between the first vessel and the second vessel.

The determination of crew social exchange 502 (see FIG. 5) may determine a risk factor for the rendezvous based on the determined risk assessment of each vessel, the time spent by each vessel in proximity to the other vessel, and the distance between the two vessels (for example, distance 1010). The determination may include a summation of risk for each point in the first vessel track 1002 with a corresponding point in second vessel track 1004.

Referring next to FIG. 11, there is shown map diagram 1100 for port visit identification in accordance with one or more embodiments. The vessel location messages or trajectory of the vessels may be received and segmented into individual trips (port to port), and may be further segmented into portions of an individual trip. The segmentation may assist in identifying the location of the vessel relative to one or more ports. The individual segments may involve determining parameters between a start point of the segment and an end point of the segment known as parameters that include distance travelled, speed, acceleration, jerk, bearing, and bearing rate.

The positional data of the vessel tracking messages may be spatially joined with different geometric location of ports, marine regions, and Exclusive Economic Zones (EEZ) encoded in shapefiles (see 408 in FIG. 4). A shapefile may be a simple, nontopological format for storing the geometric location and attribute information of geographic features. Geographic features in a shapefile may be represented by points, lines, or polygons (areas).

The marine region and EEZ shapefiles may be similar to those produced by Flander Marine Institute, which maintains a database of international borders in open waters. The EEZ may be modified or adjusted in order to improve data processing performance by reducing the size of the shapefile. This may be achieved by generating a one-way buffer in land for the EEZ. This may simplify the geometry around the coastline and allow for joining of vessel tracking messages that may be immediately at the land boundary. The buffering may also prevent an increase in the extent of a countries EEZ.

The port shapefiles may be generated using a tool, for example the World Port Index ports. The ports may be converted into points and may be buffered to generate port zone shapefiles.

The join operator between the shapefiles and vessel tracking positions may output the corresponding location identification on which each vessel tracking message is reported in. This information may be used for selecting region or geographically specific analysis (including determination of geographically specific profile data).

The vessel tracking data may be joined to a region identifier (Region ID) and a Port identifier (Port ID) to one or more segments of vessel tracking data at 408 (see FIG. 1).

A trip for a first vessel is displayed at 1102, including one or more segments. On the open ocean, the vessel tracking data is enhanced to join a region identifier (0) and port identifier (0). A region ID and a port ID of 0 may identify that the associated vessel tracking data is not associated with a particular region or port respectively. As the vessel proceeds from the ocean into the marine region defined off the coast of Turkey, the vessel tracking data may be enhanced to indicate that the vessel has entered the Iskenderun port region 1106 (noted as Port ID 44880 in port visit indication 1104). The vessel may later move to the Yakacik port region 1110, and the vessel tracking data may be enhanced to indicate that it has entered the port (noted as Port ID 44803 in port visit indication 1110).

The vessel's track/route may be visualized on a map user interface such as the one shown in map diagram 1100. The visualization may include an indication of a port visit 1104 that may include a vessel identifier (for example, the MMSI), the port identifier, a time of entry into the port, a time of exit into the port, and a number of vessel tracking messages which are received.

The second port visit to Yakacik port region may be provided as another indication of a port visit 1108 that may include a vessel identifier (for example, the MMSI), the port identifier, a time of entry into the port, a time of exit into the port, and a number of vessel tracking messages which are received.

Figure 12:
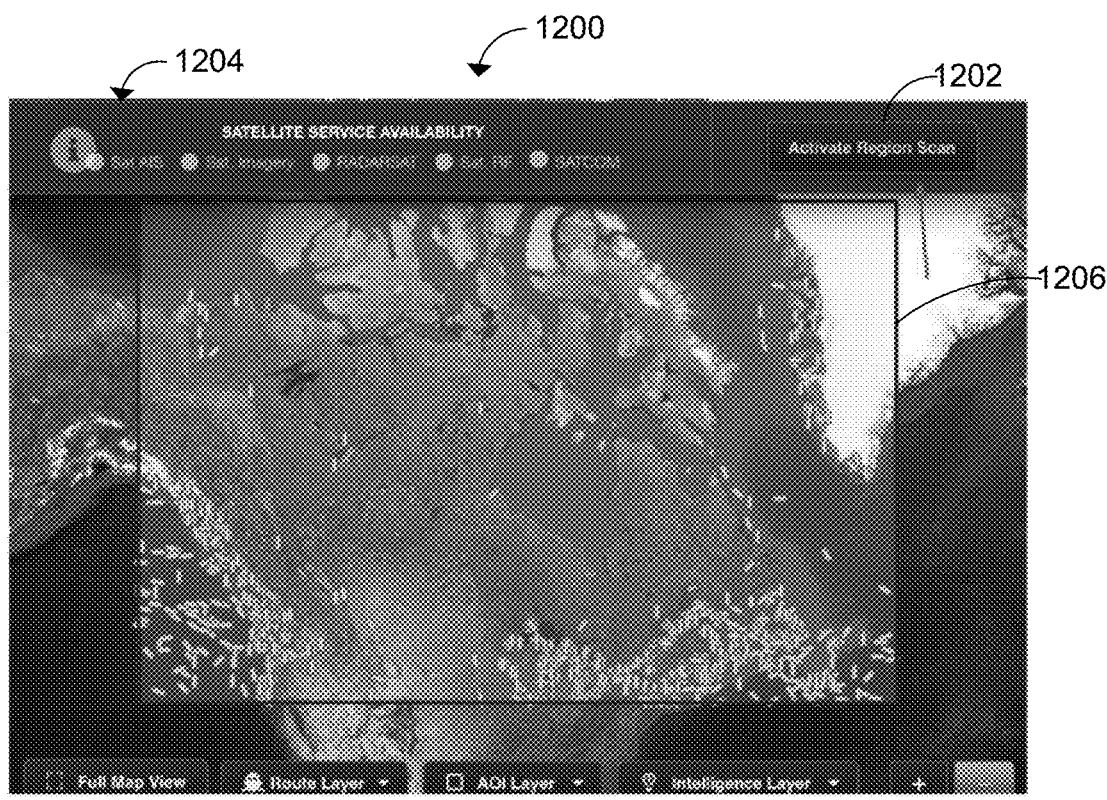
FIG. 12 shows a user interface diagram in accordance with one or more embodiments.

Referring next to FIG. 12, there is shown a user interface diagram 1200 in accordance with one or more embodiments. The user interface 1200 may be generated by the user interface engine 614 (see FIG. 6) and may be provided to an end user by way of a downloaded app on their user device in communication with server 108 (see FIG. 1), or by way of a web interface provided by server 108 (see FIG. 1).

The user interface 1200 may show a map including one or more maritime regions, EEZs or ports and one or more vessels. Communication status 1204 with one or more data providers may be displayed. The user may proceed by selecting the "Activate Region Scan" button 1202 which may begin vessel infectious disease importation risk assessment of the one or more vessels.

The user interface 1200 may include a selectable box 1206 that may enable a user to select on the map a particular region or regions for the region scan when the "Activate Region Scan" button 1202 is selected.

Figure 13:
FIG. 13 shows another user interface diagram in accordance with one or more embodiments.

Referring next to FIG. 13, there is shown another user interface diagram 1300 in accordance with one or more embodiments. Responsive to the user's selection of the "Activate Region Scan" button 1302, infectious disease importation risk assessments may be performed on the one or more vessels in the selected marine region. The user interface 1300 may display any vessels in the one or more vessels having significant risk classification. The user may select a vessel, and may be presented with an infectious disease assessment window 1302 summarizing the reasons for the infectious disease importation risk assessment of the vessel and corresponding infectious disease importation risk assessment information.

For example, the infectious disease assessment window 1302 shows a vessel name, MMSI, vessel tracking message timestamp, ship type, risk score, and risk explanation. The infectious disease assessment window may show information related to the vessel tracking data, determined vessel profile information, vessel incident information, vessel information, and vessel disease predictions.

The risk score may be a determined confidence value of the vessel infectious disease importation risk assessment, or a score related to the overall risk score determined based on the model prediction (see FIG. 5).

The infectious disease risk explanation may show a rationale for the risk score, or one or more significant contributing parameters to the score. In this example, the risk score is 96, and the explanation is that the vessel has recently visited Libya, which may have a significant uncontrolled infectious disease outbreak.

Figure 14:
FIG. 14 shows another user interface diagram in accordance with one or more embodiments.

Referring next to FIG. 14, there is shown another user interface diagram 1400 in accordance with one or more embodiments.

The user interface diagram 1400 may be displayed when the user selects the high-risk vessel displayed in infectious disease assessment window 1302 (see FIG. 13). In response to the selection, additional summary information may be displayed in a details window 1402.

The details window 1402 may show a summary of the data associated with the vessel identified in infectious disease assessment window 1302, other vessels (for example, other vessels of the same type as the vessel identified in infectious disease assessment window 1302), and notes information.

The user may select the "Vessel Note" button 1404 in order to create, edit, or remove the entries under the Vessel Notes section of the details window 1402.

Figure 15:
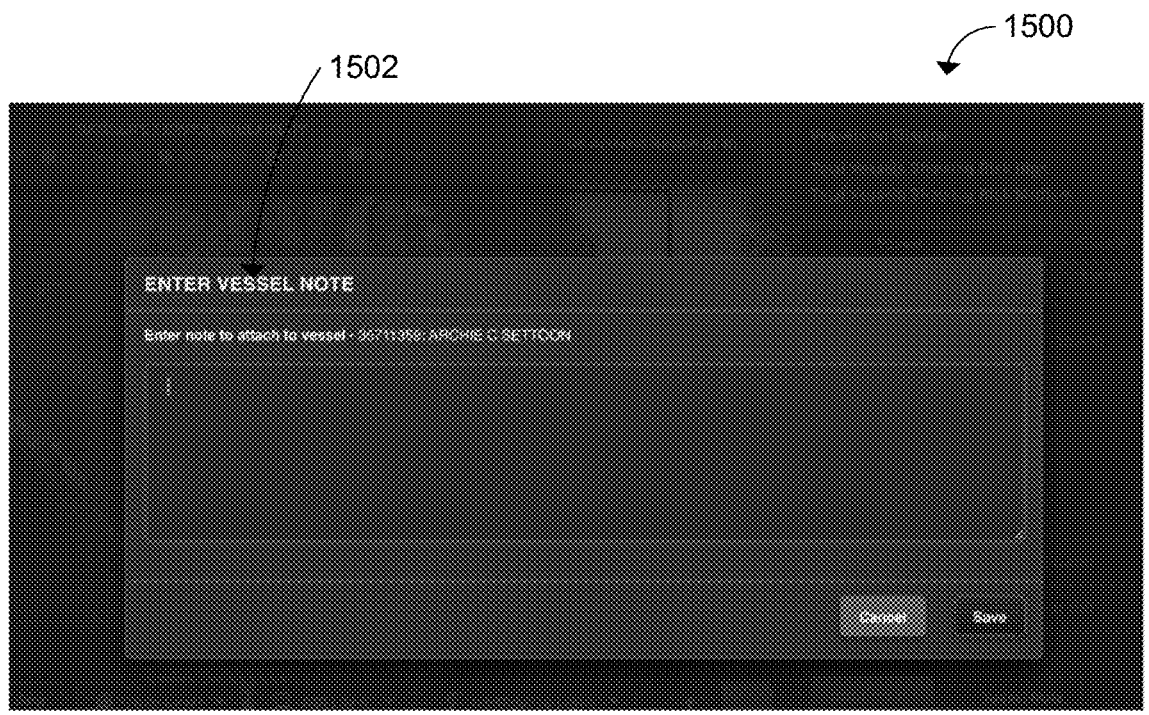
FIG. 15 shows another user interface diagram in accordance with one or more embodiments.

Referring next to FIG. 15, there is shown another user interface diagram 1500 in accordance with one or more embodiments.

Responsive to the user's selection of the "Vessel Note" button 1404, a Vessel Note window 1502 may be displayed. The vessel note window may allow for a variety of different user inputs with respect to the vessel infectious disease importation risk assessment of the vessel shown in infectious disease assessment window 1402. While a text box is shown in note window 1502, it is understood that a variety of user input types may be submitted by the user. This may allow a user to review the details of a vessel infectious disease importation risk assessment, and then submit feedback to the server 108 (see FIG. 1). In this manner, the user interface may allow for user feedback on vessel infectious disease assessments. The feedback data corresponding to the infectious disease importation risk assessment may be received by server 108, and stored in database 110 (see FIG. 1).

The present invention has been described here by way of example only. Various modification and variations may be made to these exemplary embodiments without departing from the spirit and scope of the invention, which is limited only by the appended claims.

REFERENCES

[1] Ding, X., Huang, S., Leung, A., & Rabbany, R. (2020). Incorporating Dynamic Flight Network in SEIR to Model Mobility between Populations. arXiv preprint arXiv: 2010.01408.
[2] Chande, A., Lee, S., Harris, M. et al. Real-time, interactive website for US-county-level COVID-19 event risk assessment. Nat Hum Behav 4, 1313-1319 (2020).
[3] Böhning, Dankmar, et al. "Estimating the undetected infections in the Covid-19 outbreak by harnessing capture-recapture methods." International Journal of Infectious Diseases 97 (2020): 197-201

We claim:
1. A computer-implemented method for determining an infectious disease importation risk assessment associated with a vessel, the method comprising:
   receiving, at a processor, vessel data from one or more sources, wherein the vessel data includes infectious disease data, the vessel data further comprising vessel tracking data received from a vessel tracking device associated with the vessel, the vessel tracking data comprising a plurality of Automatic Identification System (AIS) messages, the vessel tracking device comprising an AIS transceiver associated with the vessel, the one or more sources comprising at least one vessel tracking system;
   receiving, at the processor, updated vessel data from the one or more sources, the updated vessel data comprising data collected subsequent to the vessel data;
   determining, at the processor, a rendezvous history of the vessel based on the vessel data and the updated vessel data;
   determining, at the processor, a port visits history of the vessel based on the vessel data and the updated vessel data;
   determining, at the processor, a vessel disease burden based on the port visits history, the rendezvous history, the infectious disease data and a period of crew social exchange outside the vessel;
   determining, at the processor, a vessel disease progression dynamics based on the vessel disease burden and a period of crew social exchange within the vessel;
   determining, at the processor, the infectious disease importation risk assessment associated with the vessel disease progression dynamics; and
   outputting a user interface comprising a map, a vessel icon positioned on the map based on the vessel tracking data, and the infectious disease importation risk assessment associated with the vessel.

2. The method of claim 1 wherein the one or more sources include a vessel information source, an AIS data source or a regional boundaries source.

3. The method of claim 1 further comprising:
   generating, at the processor, enhanced AIS data included in the vessel data with region boundaries determined from a region boundaries data included in the vessel data; and
   tagging the enhanced AIS data based on vessel identification.

4. The method of claim 1 wherein determining the rendezvous history comprises detection of unstable speed of the vessel based on the vessel data.

5. The method of claim 4, further comprising:
determining a vessel rendezvous in the rendezvous history by determining at least one route segment of the vessel; and
identifying an outlier segment in the at least one route segment of the vessel.

6. The method of claim 1 wherein determining the port visits history comprises classification of movement of the vessel based on the vessel data.

7. The method of claim 6, wherein the classification of movement comprises classification into one of a moving class, a port visit class, an anchorage class, and a hop class.

8. The method of claim 7, wherein the determining the vessel disease burden further comprises determining the vessel disease burden by correlating at least one selected from the group of the port class and the anchorage class, with the infectious disease data.

9. The method of claim 1 wherein the period of crew social exchange outside the vessel is determined based on the rendezvous history, the port visits history and a vessel crew member data included in the vessel data.

10. The method of claim 9, further comprising:
identifying one or more vessel crew changes in the vessel data;
adjusting the period of crew social exchange outside the vessel according to the one or more vessel crew changes; and
wherein the infectious disease importation risk assessment is further determined based on the one or more vessel crew changes.

11. A computer-implemented system for determining an infectious disease importation risk assessment associated with a vessel, the system comprising:
a memory;
a processor in communication with the memory, the processor configured to:
receive vessel data from one or more sources, wherein the vessel data includes infectious disease data, the vessel data further comprising vessel tracking data received from a vessel tracking device associated with the vessel, the vessel tracking data comprising a plurality of Automatic Identification System (AIS) messages, the vessel tracking device comprising an AIS transceiver associated with the vessel, the one or more sources comprising at least one vessel tracking system;
receive updated vessel data from the one or more sources, the updated vessel data comprising data collected subsequent to the vessel data;
determine a rendezvous history of the vessel based on the vessel data and the updated vessel data;
determine a port visits history of the vessel based on the vessel data and the updated vessel data;
determine a vessel disease burden based on the port visits history, the rendezvous history, the infectious disease data and a period of crew social exchange outside the vessel;
determine a vessel disease progression dynamics based on the vessel disease burden and the vessel estimated time of arrival;
determine the infectious disease importation risk assessment associated with the vessel disease progression dynamics; and
output a user interface comprising a map, a vessel icon positioned on the map based on the vessel tracking data, and the infectious disease importation risk assessment associated with the vessel.

12. The system of claim 11 wherein the one or more sources include a vessel information source, an AIS data source or a regional boundaries source.

13. The system of claim 11 wherein the processor is further configured to:
generate enhanced AIS data included in the vessel data with region boundaries determined from a region boundaries data included in the vessel data; and
tag the enhanced AIS data based on vessel identification.

14. The system of claim 11, wherein determining the rendezvous history comprises detection of unstable speed of the vessel based on the vessel data.

15. The system of claim 14, wherein the processor is further configured to:
determine a vessel rendezvous in the rendezvous history by determining at least one route segment of the vessel; and
identifying an outlier segment in the at least one route segment of the vessel.

16. The system of claim 11, wherein determining the port visits history comprises classification of movement of the vessel based on the vessel data.

17. The system of claim 16, wherein the classification of movement comprises classification into one of a moving class, a port visit class, an anchorage class, and a hop class.

18. The system of claim 17, wherein the determining the vessel disease burden further comprises determining the vessel disease burden by correlating at least one selected from the group of the port class and the anchorage class, with the infectious disease data.

19. The system of claim 11 wherein the period of crew social exchange outside the vessel is determined based on the rendezvous history, the port visits history and a vessel crew member data included in the vessel data.

20. The system of claim 19, wherein the processor is further configured to:
identify one or more vessel crew changes in the vessel data;
adjust the period of crew social exchange outside vessel according to the one or more vessel crew changes; and
wherein the infectious disease importation risk assessment is further determined based on the one or more vessel crew changes.

* * * * *